US012708748B2

(12) United States Patent
Howell

(10) Patent No.: US 12,708,748 B2
(45) Date of Patent: Aug. 18, 2026

(54) RAPIDLY INSERTABLE CENTRAL CATHETERS INCLUDING CATHETER ASSEMBLIES AND METHODS THEREOF

(71) Applicant: Bard Access Systems, Inc., Salt Lake City, UT (US)

(72) Inventor: Glade H. Howell, Draper, UT (US)

(73) Assignee: Bard Access Systems, Inc., Salt Lake City, UT (US)

( * ) Notice: Subject to any disclaimer, the term of this patent is extended or adjusted under 35 U.S.C. 154(b) by 492 days.

(21) Appl. No.: 17/240,591

(22) Filed: Apr. 26, 2021

(65) Prior Publication Data

US 2021/0330942 A1 Oct. 28, 2021

Related U.S. Application Data

(60) Provisional application No. 63/016,085, filed on Apr. 27, 2020.

(51) Int. Cl.

*A61M 25/06* (2006.01)
*A61M 25/00* (2006.01)
*A61M 25/09* (2006.01)

(52) U.S. Cl.

CPC ...... *A61M 25/0631* (2013.01); *A61M 25/007* (2013.01); *A61M 25/09* (2013.01)

(58) Field of Classification Search

CPC .......... A61M 25/0111; A61M 25/0097; A61M 25/007; A61M 25/0029; A61M 25/0065; A61M 39/10; A61M 39/105

See application file for complete search history.

(56) References Cited

U.S. PATENT DOCUMENTS 1,013,691 A 1/1912 Shields
3,225,762 A 12/1965 Guttman
(Continued)

FOREIGN PATENT DOCUMENTS

DE 202012006191 U1 7/2012
EP 0653220 A1 5/1995
(Continued)

OTHER PUBLICATIONS

PCT/US2021/028683 filed Apr. 22, 2021 International Search Report and Written Opinion dated Sep. 16, 2021.
(Continued)

*Primary Examiner* — Bhisma Mehta
*Assistant Examiner* — Adam J. Cermak
(74) *Attorney, Agent, or Firm* — Rutan & Tucker LLP

(57) ABSTRACT

Rapidly insertable central catheters ("RICCs") including catheter assemblies and methods thereof reduce both steps and medical devices involved in introducing a catheter. A RICC assembly can include a RICC, an introducer, and a coupling system coupling the RICC and the introducer together. A catheter tube of the RICC can include a side aperture in a distal-end portion of the catheter tube, which opens into an introducing lumen extending from the side aperture to a distal end of the RICC. The introducer can include an introducer needle having a cannula. The coupling system can include a distal coupler slidably attached to the catheter tube. The cannula can extend through a longitudinal through hole of the distal coupler, through the side aperture of the catheter tube, along the introducing lumen of the catheter tube, and through the distal end of the RICC when the RICC assembly is in a ready-to-deploy state thereof.

24 Claims, 7 Drawing Sheets

(56) References Cited

U.S. PATENT DOCUMENTS 3,325,061 A 6/1967 Ellsworth
3,382,872 A * 5/1968 Rubin ................ A61M 25/065 604/161
3,570,485 A 3/1971 Reilly
3,890,976 A 6/1975 Bazell et al.
3,991,762 A 11/1976 Radford
4,205,675 A * 6/1980 Vaillancourt ...... A61M 25/0111 604/533
4,292,970 A 10/1981 Hession, Jr.
4,445,893 A 5/1984 Bodicky
4,468,224 A 8/1984 Enzmann et al.
4,484,915 A 11/1984 Tartaglia
4,525,157 A 6/1985 Vaillancourt
4,581,019 A 4/1986 Curelaru et al.
4,582,181 A 4/1986 Samson
4,594,073 A 6/1986 Stine
4,702,735 A 10/1987 Luther et al.
4,743,265 A 5/1988 Whitehouse et al.
4,766,908 A 8/1988 Clement
4,863,432 A 9/1989 Kvalo
4,935,008 A 6/1990 Lewis, Jr.
4,950,252 A 8/1990 Luther et al.
4,957,489 A 9/1990 Cameron et al.
4,994,040 A 2/1991 Cameron et al.
5,017,259 A 5/1991 Kohsai
5,040,548 A 8/1991 Yock
5,057,073 A 10/1991 Martin
5,112,312 A 5/1992 Luther
5,115,816 A 5/1992 Lee
5,120,317 A * 6/1992 Luther ............. A61M 25/0631 604/164.11
5,158,544 A 10/1992 Weinstein
5,167,634 A 12/1992 Corrigan, Jr. et al.
5,188,593 A 2/1993 Martin
5,195,962 A 3/1993 Martin et al.
5,207,650 A 5/1993 Martin
RE34,416 E * 10/1993 Lemieux .......... A61M 25/0618 604/164.08
5,267,958 A 12/1993 Buchbinder et al.
5,290,241 A 3/1994 Kraus et al.
5,292,309 A 3/1994 Van Tassel et al.
5,295,970 A 3/1994 Clinton et al.
5,306,247 A 4/1994 Pfenninger
5,312,361 A 5/1994 Zadini et al.
5,322,512 A 6/1994 Mohiuddin
5,328,472 A 7/1994 Steinke et al.
5,350,358 A 9/1994 Martin
5,358,495 A 10/1994 Lynn
5,364,355 A 11/1994 Alden et al.
5,368,567 A 11/1994 Lee
5,378,230 A 1/1995 Mahurkar
5,380,290 A 1/1995 Makower et al.
5,389,087 A 2/1995 Miraki
5,439,449 A * 8/1995 Mapes ............. A61M 25/0693 604/264
5,443,457 A 8/1995 Ginn et al.
5,460,185 A * 10/1995 Johnson ............. A61M 25/013 600/585
5,489,271 A 2/1996 Andersen
5,573,520 A 11/1996 Schwartz et al.
5,584,813 A 12/1996 Livingston et al.
5,662,622 A 9/1997 Gore et al.
5,683,370 A 11/1997 Luther et al.
5,713,876 A * 2/1998 Bogert ............. A61M 25/0631 604/243
5,718,678 A 2/1998 Fleming, III
5,772,636 A 6/1998 Brimhall et al.
5,885,251 A * 3/1999 Luther ............. A61M 25/0637 604/164.11
5,919,164 A 7/1999 Andersen
5,921,971 A * 7/1999 Agro ................ A61M 25/0029 604/523
5,947,940 A 9/1999 Beisel
5,951,518 A 9/1999 Licata et al.
5,957,893 A 9/1999 Luther et al.
5,971,957 A 10/1999 Luther et al.
6,159,198 A 12/2000 Gardeski et al.
6,197,007 B1 3/2001 Thorne et al.
6,206,849 B1 * 3/2001 Martin ............. A61M 25/0026 604/523
6,228,062 B1 * 5/2001 Howell ............ A61M 25/0668 604/165.01
6,273,874 B1 8/2001 Parris
6,475,187 B1 11/2002 Gerberding
6,533,782 B2 3/2003 Howell et al.
6,551,284 B1 * 4/2003 Greenberg ........... A61M 25/02 604/174
6,606,515 B1 8/2003 Windheuser et al.
6,616,630 B1 * 9/2003 Woehr ............. A61M 25/0625 604/110
6,626,868 B1 9/2003 Prestidge et al.
6,626,869 B1 * 9/2003 Bint ............... A61M 25/09041 604/164.01
6,638,252 B2 * 10/2003 Moulton .......... A61M 25/0612 604/533
6,716,228 B2 4/2004 Tal
6,726,659 B1 4/2004 Stocking et al.
6,819,951 B2 11/2004 Patel et al.
6,821,287 B1 11/2004 Jang
6,926,692 B2 8/2005 Katoh et al.
6,962,575 B2 11/2005 Tal
6,991,625 B1 1/2006 Gately et al.
6,994,693 B2 2/2006 Tal
6,999,809 B2 2/2006 Currier et al.
7,025,746 B2 4/2006 Tal
7,029,467 B2 4/2006 Currier et al.
7,037,293 B2 5/2006 Carrillo et al.
7,074,231 B2 7/2006 Jang
7,094,222 B1 8/2006 Siekas et al.
7,141,050 B2 11/2006 Deal et al.
7,144,386 B2 12/2006 Korkor et al.
7,311,697 B2 12/2007 Osborne
7,364,566 B2 4/2008 Elkins et al.
7,377,910 B2 * 5/2008 Katoh .............. A61M 25/0084 604/164.13
7,390,323 B2 6/2008 Jang
D600,793 S 9/2009 Bierman et al.
D601,242 S 9/2009 Bierman et al.
D601,243 S 9/2009 Bierman et al.
7,594,911 B2 9/2009 Powers et al.
7,691,093 B2 * 4/2010 Brimhall .......... A61M 25/0693 604/506
7,722,567 B2 5/2010 Tal
D617,893 S 6/2010 Bierman et al.
D624,643 S 9/2010 Bierman et al.
7,819,889 B2 * 10/2010 Healy ............. A61B 17/12022 604/161
7,857,788 B2 12/2010 Racz
D630,729 S 1/2011 Bierman et al.
7,909,797 B2 3/2011 Kennedy, II et al.
7,909,811 B2 * 3/2011 Agro ................ A61M 25/0169 604/523
7,922,696 B2 4/2011 Tal et al.
7,938,820 B2 5/2011 Webster et al.
7,967,834 B2 6/2011 Tal et al.
7,976,511 B2 7/2011 Fojtik
7,985,204 B2 7/2011 Katoh et al.
8,073,517 B1 12/2011 Burchman
8,105,286 B2 1/2012 Anderson et al.
8,192,402 B2 6/2012 Anderson et al.
8,202,251 B2 6/2012 Bierman et al.
8,206,356 B2 6/2012 Katoh et al.
8,361,011 B2 * 1/2013 Mendels .............. A61M 39/10 604/80
8,372,107 B2 2/2013 Tupper
8,377,006 B2 2/2013 Tal et al.
8,454,577 B2 6/2013 Joergensen et al.
8,585,858 B2 11/2013 Kronfeld et al.
8,657,790 B2 * 2/2014 Tal .................... A61M 25/0618 604/164.08
8,672,888 B2 3/2014 Tal
8,696,645 B2 4/2014 Tal et al.

(56) References Cited

U.S. PATENT DOCUMENTS 8,784,362 B2 7/2014 Boutilette et al.
8,827,958 B2 9/2014 Bierman et al.
8,876,704 B2 11/2014 Golden et al.
8,882,713 B1 * 11/2014 Call .................... A61M 25/09 604/164.01
8,900,192 B2 * 12/2014 Anderson ......... A61M 25/0612 604/165.02
8,900,207 B2 12/2014 Uretsky
8,915,884 B2 12/2014 Tal et al.
8,956,327 B2 2/2015 Bierman et al.
9,023,093 B2 5/2015 Pal
9,067,023 B2 6/2015 Bertocci
9,126,012 B2 9/2015 McKinnon et al.
9,138,252 B2 9/2015 Bierman et al.
9,180,275 B2 11/2015 Helm
9,265,920 B2 2/2016 Rundquist et al.
9,272,121 B2 3/2016 Piccagli
9,445,734 B2 * 9/2016 Grunwald .............. A61B 5/742
9,522,254 B2 12/2016 Belson
9,554,785 B2 1/2017 Walters et al.
9,566,087 B2 2/2017 Bierman et al.
9,675,784 B2 6/2017 Belson
9,713,695 B2 * 7/2017 Bunch .................. A61M 25/01
9,764,117 B2 9/2017 Bierman et al.
9,770,573 B2 9/2017 Golden et al.
9,814,861 B2 11/2017 Boutillette et al.
9,820,845 B2 11/2017 Von Lehe et al.
9,861,383 B2 1/2018 Clark
9,872,971 B2 1/2018 Blanchard
9,884,169 B2 2/2018 Bierman et al.
9,889,275 B2 2/2018 Voss et al.
9,913,585 B2 3/2018 McCaffrey et al.
9,913,962 B2 * 3/2018 Tal .................... A61M 25/0068
9,981,113 B2 5/2018 Bierman
10,010,312 B2 * 7/2018 Tegels ............... A61B 17/0057
10,065,020 B2 9/2018 Gaur
10,086,170 B2 10/2018 Chhikara et al.
10,098,724 B2 10/2018 Adams et al.
10,111,683 B2 10/2018 Tsamir et al.
10,118,020 B2 11/2018 Avneri et al.
10,130,269 B2 11/2018 McCaffrey et al.
10,220,184 B2 3/2019 Clark
10,220,191 B2 3/2019 Belson et al.
10,265,508 B2 4/2019 Baid
10,271,873 B2 4/2019 Steingisser et al.
10,376,675 B2 8/2019 Mitchell et al.
10,675,440 B2 6/2020 Abitabilo et al.
10,688,281 B2 6/2020 Blanchard et al.
10,806,901 B2 10/2020 Burkholz et al.
10,926,060 B2 2/2021 Stern et al.
11,260,206 B2 3/2022 Stone et al.
11,400,260 B2 8/2022 Huang et al.
11,759,607 B1 * 9/2023 Biancarelli ......... A61M 25/007 604/266
2002/0040231 A1 4/2002 Wysoki
2002/0045843 A1 4/2002 Barker et al.
2002/0123755 A1 9/2002 Lowe et al.
2002/0198492 A1 12/2002 Miller et al.
2003/0036712 A1 2/2003 Heh et al.
2003/0060863 A1 3/2003 Dobak
2003/0088212 A1 5/2003 Tal
2003/0100849 A1 5/2003 Jang
2003/0153874 A1 8/2003 Tal
2003/0158514 A1 8/2003 Tal
2004/0015138 A1 1/2004 Currier et al.
2004/0049157 A1 3/2004 Plishka et al.
2004/0064086 A1 * 4/2004 Gottlieb ............ A61M 25/0032 604/43
2004/0092879 A1 5/2004 Kraus et al.
2004/0116864 A1 6/2004 Boudreaux
2004/0116901 A1 6/2004 Appling
2004/0167478 A1 * 8/2004 Mooney ............ A61M 25/0097 604/264
2004/0193093 A1 9/2004 Desmond
2004/0230178 A1 11/2004 Wu
2005/0004554 A1 1/2005 Osborne
2005/0120523 A1 * 6/2005 Schweikert ......... A61M 39/105 24/552
2005/0131343 A1 6/2005 Abrams et al.
2005/0148936 A1 7/2005 Moss
2005/0215956 A1 9/2005 Nerney
2005/0215958 A1 9/2005 Hawthorne
2005/0245882 A1 11/2005 Elkins et al.
2005/0283221 A1 12/2005 Mann et al.
2006/0009740 A1 1/2006 Higgins et al.
2006/0116629 A1 6/2006 Tal et al.
2006/0129100 A1 6/2006 Tal
2006/0129130 A1 6/2006 Tal et al.
2006/0135973 A1 6/2006 Hawkins et al.
2007/0276288 A1 11/2007 Khaw
2008/0045894 A1 2/2008 Perchik et al.
2008/0091137 A1 4/2008 Reavill
2008/0125744 A1 5/2008 Treacy
2008/0125748 A1 5/2008 Patel
2008/0132850 A1 6/2008 Fumiyama et al.
2008/0262430 A1 10/2008 Anderson et al.
2008/0262431 A1 10/2008 Anderson et al.
2008/0294111 A1 11/2008 Tal et al.
2008/0312578 A1 12/2008 DeFonzo et al.
2008/0319387 A1 12/2008 Amisar et al.
2009/0131872 A1 5/2009 Popov
2009/0187147 A1 7/2009 Kurth et al.
2009/0221961 A1 9/2009 Tal et al.
2009/0270889 A1 10/2009 Tal et al.
2009/0292272 A1 11/2009 McKinnon
2010/0030154 A1 * 2/2010 Duffy ................ A61M 25/0668 604/161
2010/0256487 A1 10/2010 Hawkins et al.
2010/0298839 A1 * 11/2010 Castro ................ A61B 17/3421 604/164.05
2010/0305474 A1 12/2010 DeMars et al.
2011/0004162 A1 1/2011 Tal
2011/0009827 A1 1/2011 Bierman et al.
2011/0021994 A1 1/2011 Anderson et al.
2011/0066142 A1 3/2011 Tal et al.
2011/0071502 A1 3/2011 Asai
2011/0144620 A1 6/2011 Tal
2011/0152836 A1 6/2011 Riopelle et al.
2011/0190778 A1 8/2011 Arpasi et al.
2011/0202006 A1 8/2011 Bierman et al.
2011/0230844 A1 9/2011 Shaw et al.
2011/0251559 A1 10/2011 Tal et al.
2011/0270192 A1 11/2011 Anderson et al.
2012/0016346 A1 1/2012 Steinmetz et al.
2012/0041371 A1 2/2012 Tal et al.
2012/0065590 A1 3/2012 Bierman et al.
2012/0078231 A1 3/2012 Hoshinouchi
2012/0130411 A1 5/2012 Tal et al.
2012/0130415 A1 5/2012 Tal et al.
2012/0157854 A1 6/2012 Kurrus et al.
2012/0215171 A1 8/2012 Christiansen
2012/0220942 A1 8/2012 Hall et al.
2012/0226239 A1 9/2012 Green
2012/0283640 A1 11/2012 Anderson et al.
2012/0316500 A1 12/2012 Bierman et al.
2013/0046241 A1 2/2013 Okamura et al.
2013/0053763 A1 2/2013 Makino et al.
2013/0053826 A1 2/2013 Shevgoor
2013/0123704 A1 5/2013 Bierman et al.
2013/0158338 A1 6/2013 Kelly et al.
2013/0158506 A1 6/2013 Harris et al.
2013/0188291 A1 7/2013 Vardiman
2013/0237931 A1 9/2013 Tal et al.
2013/0306079 A1 11/2013 Tracy
2014/0025036 A1 1/2014 Bierman et al.
2014/0081210 A1 3/2014 Bierman et al.
2014/0094774 A1 4/2014 Blanchard
2014/0100552 A1 * 4/2014 Gallacher ............ A61M 39/20 604/528
2014/0110296 A1 4/2014 Terzibashian
2014/0171833 A1 6/2014 Matsuno et al.
2014/0188211 A1 7/2014 Roeder et al.
2014/0207052 A1 7/2014 Tal et al.

(56) References Cited

U.S. PATENT DOCUMENTS

2014/0207069 A1 7/2014 Bierman et al.
2014/0214005 A1 7/2014 Belson
2014/0221831 A1 8/2014 Kurrus et al.
2014/0257111 A1 9/2014 Yamashita et al.
2014/0276432 A1 9/2014 Bierman et al.
2014/0276599 A1 9/2014 Cully et al.
2014/0364766 A1 12/2014 Devgon et al.
2015/0011834 A1 1/2015 Ayala et al.
2015/0080939 A1 3/2015 Adams et al.
2015/0094653 A1* 4/2015 Pacheco ................ A61B 34/30 604/95.01
2015/0112307 A1 4/2015 Margolis
2015/0112310 A1* 4/2015 Call ..................... A61M 39/10 604/528
2015/0119806 A1 4/2015 Blanchard et al.
2015/0126930 A1 5/2015 Bierman et al.
2015/0148595 A1 5/2015 Bagwell et al.
2015/0157829 A1 6/2015 Bunch et al.
2015/0190168 A1 7/2015 Bierman et al.
2015/0196210 A1 7/2015 McCaffrey et al.
2015/0224287 A1 8/2015 Bian et al.
2015/0231364 A1 8/2015 Blanchard et al.
2015/0283357 A1 10/2015 Lampropoulos et al.
2015/0290431 A1 10/2015 Hall et al.
2015/0297868 A1 10/2015 Tal et al.
2015/0306356 A1 10/2015 Gill
2015/0320969 A1 11/2015 Haslinger et al.
2015/0320977 A1 11/2015 Vitullo et al.
2015/0351793 A1 12/2015 Bierman et al.
2015/0359549 A1 12/2015 Lenker et al.
2015/0359998 A1 12/2015 Carmel et al.
2016/0001046 A1 1/2016 Tietze
2016/0030716 A1 2/2016 Mallin et al.
2016/0067391 A1 3/2016 Real et al.
2016/0082223 A1 3/2016 Barnell
2016/0114124 A1 4/2016 Tal
2016/0158523 A1* 6/2016 Helm .................... A61M 39/18 604/513
2016/0220786 A1* 8/2016 Mitchell ........... A61M 25/0029
2016/0220811 A1 8/2016 Spotnitz et al.
2016/0242661 A1 8/2016 Fischell et al.
2016/0256101 A1 9/2016 Aharoni et al.
2016/0256667 A1 9/2016 Ribelin et al.
2016/0325073 A1 11/2016 Davies et al.
2016/0331938 A1 11/2016 Blanchard et al.
2016/0338728 A1 11/2016 Tal
2016/0346503 A1 12/2016 Jackson et al.
2017/0028135 A1 2/2017 Fransson et al.
2017/0035990 A1 2/2017 Swift
2017/0072165 A1 3/2017 Lim et al.
2017/0120000 A1* 5/2017 Osypka ............... A61M 39/105
2017/0120014 A1* 5/2017 Harding ................ A61M 39/04
2017/0120034 A1* 5/2017 Kaczorowski ..... A61B 17/3423
2017/0128700 A1 5/2017 Roche Rebollo
2017/0156987 A1* 6/2017 Babbs .............. A61M 39/0247
2017/0172653 A1 6/2017 Urbanski et al.
2017/0182293 A1 6/2017 Chhikara et al.
2017/0239443 A1 8/2017 Abitabilo et al.
2017/0259043 A1 9/2017 Chan et al.
2017/0273713 A1 9/2017 Shah et al.
2017/0274182 A1 9/2017 O'Bryan et al.
2017/0296792 A1 10/2017 Ornelas Vargas et al.
2017/0326339 A1 11/2017 Bailey et al.
2017/0361070 A1 12/2017 Hivert
2017/0368255 A1* 12/2017 Provost ................ G02B 27/425
2018/0001062 A1 1/2018 O'Carrol et al.
2018/0008294 A1 1/2018 Garrison et al.
2018/0021545 A1 1/2018 Mitchell et al.
2018/0116690 A1 5/2018 Sarabia et al.
2018/0117284 A1 5/2018 Appling et al.
2018/0133438 A1 5/2018 Hulvershorn et al.
2018/0154062 A1 6/2018 DeFonzo et al.
2018/0154112 A1* 6/2018 Chan ................ A61M 25/0606
2018/0214674 A1* 8/2018 Ebnet ................ A61M 25/0606
2018/0229004 A1 8/2018 Blanchard et al.
2018/0296799 A1 10/2018 Horst et al.
2018/0296804 A1 10/2018 Bierman
2018/0310955 A1 11/2018 Lindekugel et al.
2018/0369540 A1 12/2018 Asai
2019/0015646 A1 1/2019 Matlock et al.
2019/0021640 A1 1/2019 Burkholz et al.
2019/0038113 A1 2/2019 Chu
2019/0060616 A1 2/2019 Solomon
2019/0076167 A1 3/2019 Fantuzzi et al.
2019/0076628 A1 3/2019 Anstett
2019/0134349 A1 5/2019 Cohn et al.
2019/0192824 A1 6/2019 Cordeiro et al.
2019/0201665 A1* 7/2019 Turpin ................ A61M 5/1413
2019/0209812 A1* 7/2019 Burkholz .......... A61M 25/0606
2019/0240459 A1 8/2019 Belson
2019/0255294 A1 8/2019 Mitchell et al.
2019/0255298 A1* 8/2019 Mitchell ........... A61M 25/0097
2019/0275303 A1 9/2019 Tran et al.
2019/0276268 A1 9/2019 Akingba
2019/0282788 A1 9/2019 Stone et al.
2019/0321590 A1 10/2019 Burkholz et al.
2019/0351196 A1 11/2019 Ribelin et al.
2020/0001051 A1 1/2020 Huang et al.
2020/0016374 A1* 1/2020 Burkholz ........... A61M 25/0113
2020/0046948 A1 2/2020 Burkholz et al.
2020/0100716 A1* 4/2020 Devgon ........... A61B 5/150732
2020/0129732 A1* 4/2020 Vogt .................... A61M 25/007
2020/0147349 A1 5/2020 Holt
2020/0197579 A1 6/2020 Chu et al.
2020/0197682 A1* 6/2020 Franklin ........... A61M 25/0097
2020/0197684 A1* 6/2020 Wax ...................... A61M 39/20
2020/0237278 A1 7/2020 Asbaghi
2020/0359995 A1* 11/2020 Walsh .................. A61B 8/4461
2021/0030944 A1* 2/2021 Cushen ............... A61M 3/0279
2021/0060306 A1 3/2021 Kumar
2021/0069471 A1 3/2021 Howell
2021/0085927 A1 3/2021 Howell
2021/0100985 A1 4/2021 Akcay et al.
2021/0113809 A1 4/2021 Howell
2021/0113810 A1 4/2021 Howell
2021/0113816 A1 4/2021 DiCianni
2021/0121661 A1 4/2021 Howell
2021/0121667 A1 4/2021 Howell
2021/0228842 A1 7/2021 Scherich et al.
2021/0228843 A1 7/2021 Howell et al.
2021/0244920 A1 8/2021 Kujawa et al.
2021/0290898 A1* 9/2021 Burkholz ............ A61M 25/007
2021/0290901 A1* 9/2021 Burkholz .......... A61M 25/0075
2021/0290913 A1* 9/2021 Horst .................... A61M 25/09
2021/0322729 A1 10/2021 Howell
2021/0330941 A1 10/2021 Howell et al.
2021/0361915 A1 11/2021 Howell et al.
2021/0402149 A1 12/2021 Howell
2021/0402153 A1 12/2021 Howell et al.
2022/0001109 A1 1/2022 Simon
2022/0001138 A1 1/2022 Howell
2022/0032013 A1 2/2022 Howell et al.
2022/0032014 A1 2/2022 Howell et al.
2022/0062528 A1 3/2022 Thornley et al.
2022/0062596 A1 3/2022 Ribelin et al.
2022/0126064 A1 4/2022 Tobin et al.
2022/0193376 A1 6/2022 Spataro et al.
2022/0193377 A1 6/2022 Haymond et al.
2022/0193378 A1 6/2022 Spataro et al.
2022/0203075 A1 6/2022 Murphy
2022/0323723 A1 10/2022 Spataro et al.
2022/0331562 A1 10/2022 Jaros et al.
2022/0331563 A1 10/2022 Papadia
2023/0042898 A1 2/2023 Howell et al.
2023/0096377 A1 3/2023 West et al.
2023/0096740 A1 3/2023 Bechstein et al.
2023/0099654 A1 3/2023 Blanchard et al.
2023/0100482 A1 3/2023 Howell
2023/0101455 A1 3/2023 Howell et al.
2023/0102231 A1 3/2023 Bechstein et al.
2023/0173231 A1 6/2023 Parikh et al.
2023/0233814 A1 7/2023 Howell et al.
2023/0381459 A1 11/2023 Belson et al.
2023/0381481 A1 11/2023 Pizzato

(56) References Cited

U.S. PATENT DOCUMENTS

| | | | |
|---|---|---|---|
| 2024/0009427 | A1 | 1/2024 | Howell et al. |
| 2024/0050706 | A1 | 2/2024 | Howell et al. |
| 2024/0198058 | A1 | 6/2024 | Howell et al. |
| 2025/0001136 | A1 | 1/2025 | Mitchell et al. |
| 2025/0065083 | A1 | 2/2025 | Haymond et al. |
| 2025/0082906 | A1 | 3/2025 | Howell et al. |
| 2025/0222237 | A1 | 7/2025 | Spataro et al. |
| 2025/0235669 | A1 | 7/2025 | Howell |

FOREIGN PATENT DOCUMENTS

| | | | | |
|---|---|---|---|---|
| EP | 0730880 A1 | 9/1996 | | |
| EP | 1458437 B1 | 3/2010 | | |
| EP | 2248549 A2 | 11/2010 | | |
| EP | 2319576 A1 | 5/2011 | | |
| EP | 2366422 A1 | 9/2011 | | |
| EP | 2486880 A2 | 8/2012 | | |
| EP | 2486881 A2 | 8/2012 | | |
| EP | 2486951 A2 | 8/2012 | | |
| EP | 2152348 B1 | 2/2015 | | |
| EP | 3473291 A1 | 4/2019 | | |
| EP | 3093038 B1 | 5/2019 | | |
| EP | 2260897 B1 | 9/2019 | | |
| EP | 3693051 A1 | 8/2020 | | |
| GB | 1273547 A | 5/1972 | | |
| JP | 2004248987 A | 9/2004 | | |
| JP | 2008054859 A | 3/2008 | | |
| WO | 94/21315 A1 | 9/1994 | | |
| WO | WO-9532009 A2 | * | 11/1995 | A61M 25/0693 |
| WO | 98/44979 A1 | 10/1998 | | |
| WO | 98/53871 A1 | 12/1998 | | |
| WO | 9857685 A1 | 12/1998 | | |
| WO | WO-9912600 A1 | * | 3/1999 | A61M 25/09041 |
| WO | 99/26681 A1 | 6/1999 | | |
| WO | 00/06221 A1 | 2/2000 | | |
| WO | WO-0054830 A1 | * | 9/2000 | A61M 25/02 |
| WO | 2003008020 A1 | 1/2003 | | |
| WO | 2003057272 A2 | 7/2003 | | |
| WO | 03/068073 A1 | 8/2003 | | |
| WO | 2003066125 A2 | 8/2003 | | |
| WO | 2005096778 A2 | 10/2005 | | |
| WO | 2006055780 A2 | 5/2006 | | |
| WO | WO-2006055288 A2 | * | 5/2006 | A61M 1/3661 |
| WO | 2007046850 A2 | 4/2007 | | |
| WO | 2008033983 A1 | 3/2008 | | |
| WO | 2008092029 A2 | 7/2008 | | |
| WO | 2008/131300 A2 | 10/2008 | | |
| WO | 2008131289 A2 | 10/2008 | | |
| WO | 2009114833 A1 | 9/2009 | | |
| WO | 2009114837 A2 | 9/2009 | | |
| WO | 2010/048449 A2 | 4/2010 | | |
| WO | 2010056906 A2 | 5/2010 | | |
| WO | 2010083467 A2 | 7/2010 | | |
| WO | 2010/132608 A2 | 11/2010 | | |
| WO | 2011081859 A2 | 7/2011 | | |
| WO | 2011097639 A2 | 8/2011 | | |
| WO | 2011109792 A1 | 9/2011 | | |
| WO | 2011146764 A1 | 11/2011 | | |
| WO | 2012068162 A2 | 5/2012 | | |
| WO | 2012068166 A2 | 5/2012 | | |
| WO | 2012135761 A1 | 10/2012 | | |
| WO | 2012/154277 A1 | 11/2012 | | |
| WO | 2012162677 A1 | 11/2012 | | |
| WO | 2013026045 A1 | 2/2013 | | |
| WO | 2013138519 A1 | 9/2013 | | |
| WO | 2014006403 A1 | 1/2014 | | |
| WO | 2014/100392 A1 | 6/2014 | | |
| WO | 2014113257 A2 | 7/2014 | | |
| WO | 2014152005 A2 | 9/2014 | | |
| WO | 2014197614 A2 | 12/2014 | | |
| WO | 2015057766 A1 | 4/2015 | | |
| WO | WO-2015077560 A1 | * | 5/2015 | A61M 1/3653 |
| WO | 2015/168655 A2 | 11/2015 | | |
| WO | 2016110824 A1 | 7/2016 | | |
| WO | 2016123278 A1 | 8/2016 | | |
| WO | 2016139590 A1 | 9/2016 | | |
| WO | 2016139597 A2 | 9/2016 | | |
| WO | 2016/178974 A1 | 11/2016 | | |
| WO | 2016/187063 A1 | 11/2016 | | |
| WO | 2016176065 A1 | 11/2016 | | |
| WO | 2018089285 A1 | 5/2018 | | |
| WO | 2018089385 A1 | 5/2018 | | |
| WO | WO-2018089275 A1 | * | 5/2018 | A61M 1/3653 |
| WO | 2018191547 A1 | 10/2018 | | |
| WO | 2018218236 A1 | 11/2018 | | |
| WO | WO-2018213148 A1 | * | 11/2018 | A61M 25/0606 |
| WO | 2019/050576 A1 | 3/2019 | | |
| WO | 2019/146026 A1 | 8/2019 | | |
| WO | 2019199734 A1 | 10/2019 | | |
| WO | 2020014149 A1 | 1/2020 | | |
| WO | 2020069395 A1 | 4/2020 | | |
| WO | 2020/109448 A1 | 6/2020 | | |
| WO | 2020/113123 A1 | 6/2020 | | |
| WO | 2021038041 A1 | 3/2021 | | |
| WO | 2021050302 A1 | 3/2021 | | |
| WO | 2021/077103 A1 | 4/2021 | | |
| WO | 2021062023 A1 | 4/2021 | | |
| WO | 2021081205 A1 | 4/2021 | | |
| WO | 2021086793 A1 | 5/2021 | | |
| WO | 2021/236950 A1 | 11/2021 | | |
| WO | 2021226050 A1 | 11/2021 | | |
| WO | 2022/031618 A1 | 2/2022 | | |
| WO | 2022/094141 A1 | 5/2022 | | |
| WO | 2022/133297 A1 | 6/2022 | | |
| WO | 2022-140406 A1 | 6/2022 | | |
| WO | 2022/140429 A1 | 6/2022 | | |
| WO | 2022/217098 A1 | 10/2022 | | |
| WO | 2023014994 A1 | 2/2023 | | |
| WO | 2023/049498 A1 | 3/2023 | | |
| WO | 2023049505 A1 | 3/2023 | | |
| WO | 2023049511 A1 | 3/2023 | | |
| WO | 2023049519 A1 | 3/2023 | | |
| WO | 2023049522 A1 | 3/2023 | | |
| WO | 2023/146792 A1 | 8/2023 | | |

OTHER PUBLICATIONS

PCT/US2021/029183 filed Apr. 26, 2021 International Search Report and Written Opinion dated Sep. 24, 2021.

PCT/US2021/033443 filed May 20, 2021 International Search Report and Written Opinion dated Sep. 23, 2021.

PCT/US2021/044029 filed Jul. 30, 2021 International Search Report and Written Opinion dated Dec. 9, 2021.

PCT/US2020/048583 filed Aug. 28, 2020 International Search Report and Written Opinion dated Nov. 13, 2020.

PCT/US2020/052536 filed Sep. 24, 2020 International Search Report and Written Opinion dated Dec. 4, 2020.

PCT/US2020/056364 filed Oct. 19, 2020 International Search Report and Written Opinion dated Jan. 19, 2021.

PCT/US2020/056864 filed Oct. 22, 2020 International Search Report and Written Opinion dated Jan. 14, 2021.

PCT/US2020/057202 filed Oct. 23, 2020 International Search Report and Written Opinion dated Jan. 21, 2021.

PCT/US2020/057397 filed Oct. 26, 2020 International Search Report and Written Opinion dated Mar. 10, 2021.

U.S. Appl. No. 15/008,628, filed Jan. 28, 2016 Final Office Action dated May 30, 2018.

U.S. Appl. No. 15/008,628, filed Jan. 28, 2016 Non-Final Office Action dated Jan. 25, 2019.

U.S. Appl. No. 15/008,628, filed Jan. 28, 2016 Non-Final Office Action dated Nov. 2, 2017.

U.S. Appl. No. 15/008,628, filed Jan. 28, 2016 Notice of Allowance dated May 15, 2019.

U.S. Appl. No. 16/398,020, filed Apr. 29, 2019 Non-Final Office Action dated May 11, 2021.

PCT/US2021/044223 filed Aug. 2, 2021 International Search Report and Written Opinion dated Dec. 21, 2021.

PCT/US2021/048275 filed Aug. 30, 2021 International Search Report and Written Opinion dated Jan. 4, 2022.

(56) References Cited

OTHER PUBLICATIONS

PCT/US2021/064642 filed Dec. 21, 2021 International Search Report and Written Opinion dated May 11, 2022.
U.S. Appl. No. 17/031,478, filed Sep. 24, 2020 Non-Final Office Action dated May 11, 2022.
PCT/US2021/064671 filed Dec. 21, 2021 International Search Report and Written Opinion dated May 27, 2022.
PCT/US2022/024085 filed Apr. 8, 2022 International Search Report and Wirtten Opinion dated Sep. 12, 2022.
U.S. Appl. No. 16/398,020, filed Apr. 29, 2019 Examiner's Answer dated Oct. 31, 2022.
U.S. Appl. No. 17/031,478, filed Sep. 24, 2020 Notice of Allowance dated Sep. 16, 2022.
U.S. Appl. No. 17/156,252, filed Jan. 22, 2021 Non-Final Office Action dated Oct. 25, 2022.
PCT/US2021/014700 filed Jan. 22, 2021 International Search Report and Written Opinion dated Jun. 29, 2021.
PCT/US2021/028018 filed Apr. 19, 2021 International Search Report and Written Opinion dated Sep. 13, 2021.
PCT/US2021/039084 filed Jun. 25, 2021 International Search Report and Written Opinion dated Jan. 10, 2022.
PCT/US2021/039843 filed Jun. 30, 2021 International Search Report and Written Opinion dated Nov. 11, 2021.
U.S. Appl. No. 16/398,020, filed Apr. 29, 2019 Final Office Action dated Jan. 25, 2022.
U.S. Appl. No. 17/006,553, filed Aug. 28, 2020 Non-Final Office Action dated Mar. 16, 2022.
U.S. Appl. No. 17/077,728, filed Oct. 22, 2020 Non-Final Office Action dated Feb. 9, 2022.
PCT/US2021/028018 filed Apr. 19, 2021 International Preliminary Report on Patentability dated Jun. 3, 2022.
PCT/US2021/064174 filed Dec. 17, 2021 International Search Report and Written Opinion dated May 18, 2022.
PCT/US2021/057135 filed Oct. 28, 2021 International Preliminary Report on Patentability dated May 2, 2023.
PCT/US2021/057135 filed Oct. 28, 2021 International Search Report and Written Opinion dated Mar. 11, 2022.
PCT/US2022/039614 filed Aug. 5, 2022 International Search Report and Written Opinion dated Dec. 22, 2022.
PCT/US2022/044848 filed Sep. 27, 2022 International Search Report and Written Opinion dated Feb. 3, 2023.
PCT/US2022/044879 filed Sep. 27, 2022 International Search Report and Written Opinion dated Mar. 3, 2023.
PCT/US2022/044901 filed Sep. 27, 2022 International Search Report and Written Opinion dated Mar. 3, 2023.
PCT/US2022/044918 filed Sep. 27, 2022 International Search Report and Written Opinion dated Feb. 21, 2023.
PCT/US2022/044923 filed Sep. 27, 2022 International Search Report and Written Opinion dated Feb. 15, 2023.
U.S. Appl. No. 17/156,252, filed Jan. 22, 2021 Notice of Allowance dated Apr. 24, 2023.
U.S. Appl. No. 17/237,909, filed Apr. 22, 2021 Restriction Requirement dated Feb. 1, 2023.
U.S. Appl. No. 17/326,017, filed May 20, 2021 Non-Final Office Action dated Jan. 26, 2023.
U.S. Appl. No. 17/390,682, filed Jul. 30, 2021 Non-Final Office Action dated Mar. 2, 2023.
U.S. Appl. No. 17/392,061, filed Aug. 2, 2021 Restriction Requirement dated Mar. 30, 2023.
PCT/US2023/011173 filed Jan. 19, 2023 International Search Report and Written Opinion dated May 22, 2023.
U.S. Appl. No. 17/156,252, filed Jan. 22, 2021 Notice of Allowance dated Aug. 9, 2023.
U.S. Appl. No. 17/237,909, filed Apr. 22, 2021 Non-Final Office Action dated Jul. 27, 2023.
U.S. Appl. No. 17/326,017, filed May 20, 2021 Notice of Allowance dated Jul. 3, 2023.
U.S. Appl. No. 17/358,504, filed Jun. 25, 2021 Restriction Requirement dated Jun. 7, 2023.
U.S. Appl. No. 17/360,694, filed Jun. 28, 2021 Restriction Requirement dated Jul. 20, 2023.
U.S. Appl. No. 17/390,682, filed Jul. 30, 2021 Final Office Action dated Jul. 27, 2023.
U.S. Appl. No. 17/392,061, filed Aug. 2, 2021 Non-Final Office Action dated Jul. 17, 2023.
U.S. Appl. No. 16/398,020, filed Apr. 29, 2019 Board Decision dated Oct. 30, 2023.
U.S. Appl. No. 17/237,909, filed Apr. 22, 2021 Notice of Allowance dated Oct. 27, 2023.
U.S. Appl. No. 17/358,504, filed Jun. 25, 2021 Non-Final Office Action dated Oct. 4, 2023.
U.S. Appl. No. 17/360,694, filed Jun. 28, 2021 Non-Final Office Action dated Oct. 13, 2023.
U.S. Appl. No. 17/390,682, filed Jul. 30, 2021 Non-Final Office Action dated Dec. 1, 2023.
U.S. Appl. No. 17/392,061, filed Aug. 2, 2021 Final Office Action dated Nov. 21, 2023.
U.S. Appl. No. 17/513,789, filed Oct. 28, 2021 Restriction Requirement dated Oct. 3, 2023.
U.S. Appl. No. 17/557,924, filed Dec. 21, 2021 Non-Final Office Action dated Nov. 3, 2023.
U.S. Appl. No. 16/398,020, filed Apr. 29, 2019 Non-Final Office Action dated Jan. 18, 2024.
U.S. Appl. No. 17/234,611, filed Apr. 19, 2021 Restriction Requirement dated Jan. 18, 2024.
U.S. Appl. No. 17/360,694, filed Jun. 28, 2021 Non-Final Office Action dated Feb. 14, 2024.
U.S. Appl. No. 17/392,061, filed Aug. 2, 2021 Advisory Action dated Feb. 14, 2024.
U.S. Appl. No. 17/513,789, filed Oct. 28, 2021 Non-Final Office Action dated Jan. 9, 2024.
U.S. Appl. No. 17/557,924, filed Dec. 21, 2021 Final Office Action dated Feb. 29, 2024.
U.S. Appl. No. 16/398,020, filed Apr. 29, 2019 Notice of Allowance dated May 20, 2024.
U.S. Appl. No. 17/234,611, filed Apr. 19, 2021 Non-Final Office Action dated Apr. 23, 2024.
U.S. Appl. No. 17/358,504, filed Jun. 25, 2021 Final Office Action dated Mar. 13, 2024.
U.S. Appl. No. 17/390,682, filed Jul. 30, 2021 Final Office Action dated May 6, 2024.
U.S. Appl. No. 17/392,061, filed Aug. 2, 2021 Non-Final Office Action dated Apr. 23, 2024.
U.S. Appl. No. 17/554,978, filed Dec. 17, 2021 Non-Final Office Action dated Apr. 19, 2024.
U.S. Appl. No. 17/234,611, filed Apr. 19, 2021 Final Office Action dated Sep. 20, 2024.
U.S. Appl. No. 17/358,504, filed Jun. 25, 2021 Notice of Allowance dated Jul. 17, 2024.
U.S. Appl. No. 17/390,682, filed Jul. 30, 2021 Non-Final Office Action dated Jul. 5, 2024.
U.S. Appl. No. 17/513,789, filed Oct. 28, 2021 Final Office Action dated Jul. 9, 2024.
U.S. Appl. No. 17/554,978, filed Dec. 17, 2021 Notice of Allowance dated Jul. 24, 2024.
U.S. Appl. No. 17/557,924, filed Dec. 21, 2021 Non-Final Office Action dated Aug. 20, 2024.
U.S. Appl. No. 17/558,124, filed Dec. 21, 2021 Non-Final Office Action dated Sep. 20, 2024.
U.S. Appl. No. 17/234,611, filed Apr. 19, 2021 Examiner's Answer dated May 1, 2025.
U.S. Appl. No. 17/392,061, filed Aug. 2, 2021 Advisory Action dated Mar. 12, 2025.
U.S. Appl. No. 17/392,061, filed Aug. 2, 2021 Non-Final Office Action dated Apr. 5, 2025.
U.S. Appl. No. 17/558,124, filed Dec. 21, 2021 Notice of Allowance dated Mar. 7, 2025.
U.S. Appl. No. 17/234,611, filed Apr. 19, 2021 Board Decision dated Jan. 23, 2026.
U.S. Appl. No. 17/390,682, filed Jul. 30, 2021 Notice of Allowance dated Dec. 15, 2025.

(56) References Cited

OTHER PUBLICATIONS

U.S. Appl. No. 17/882,388, filed Aug. 5, 2022 Final Office Action dated Jan. 12, 2026.
U.S. Appl. No. 17/953,663, filed Sep. 27, 2022 Non-Final Office Action dated Jan. 22, 2026.
U.S. Appl. No. 17/953,860, filed Sep. 27, 2022 Non-Final Office Action dated Jan. 29, 2026.
U.S. Appl. No. 17/954,096, filed Sep. 27, 2022 Final Office Action dated Feb. 10, 2026.
U.S. Appl. No. 17/954,132, filed Sep. 27, 2022 Final Office Action dated Mar. 4, 2026.
U.S. Appl. No. 18/372,610, filed Sep. 25, 2023 Notice of Allowance dated Dec. 16, 2025.
U.S. Appl. No. 18/383,814, filed Oct. 25, 2023 Restriction Requirement dated Jan. 22, 2026.
U.S. Appl. No. 17/392,061, filed Aug. 2, 2021 Notice of Allowance dated Oct. 27, 2025.
U.S. Appl. No. 17/461,619, filed Aug. 30, 2021 Non-Final Office Action dated Oct. 7, 2025.
U.S. Appl. No. 17/716,675, filed Apr. 8, 2022 Non-Final Office Action dated Sep. 11, 2025.
U.S. Appl. No. 17/953,663, filed Sep. 27, 2022 Restriction Requirement dated Oct. 3, 2025.
U.S. Appl. No. 17/953,860, filed Sep. 27, 2022 Restriction Requirement dated Oct. 22, 2025.
U.S. Appl. No. 17/953,959, filed Sep. 27, 2022 Restriction Requirement dated Oct. 22, 2025.
U.S. Appl. No. 18/099,185, filed Jan. 19, 2023 Non-Final Office Action dated Dec. 2, 2025.
U.S. Appl. No. 17/461,619, filed Aug. 30, 2021 Advisory Action dated Aug. 14, 2025.
U.S. Appl. No. 17/461,619, filed Aug. 30, 2021 Final Office Action dated Jun. 2, 2025.
U.S. Appl. No. 17/716,675, filed Apr. 8, 2022 Restriction Requirement dated Jul. 2, 2025.
U.S. Appl. No. 17/882,388, filed Aug. 5, 2022 Non-Final Office Action dated Aug. 20, 2025.
U.S. Appl. No. 17/954,096, filed Sep. 27, 2022 Non-Final Office Action dated Aug. 26, 2025.
U.S. Appl. No. 17/954,132, filed Sep. 27, 2022 Non-Final Office Action dated Aug. 21, 2025.
U.S. Appl. No. 17/461,619, filed Aug. 30, 2021 Non-Final Office Action dated Feb. 11, 2025.
U.S. Appl. No. 17/513,789, filed Oct. 28, 2021 Notice of Allowance dated Jan. 3, 2025.
U.S. Appl. No. 17/716,675, filed Apr. 8, 2022 Non-Final Office Action dated Mar. 9, 2026.
U.S. Appl. No. 17/882,388, filed Aug. 5, 2022 Notice of Allowance dated Apr. 13, 2026.
U.S. Appl. No. 17/953,959, filed Sep. 27, 2022 Non-Final Office Action dated Mar. 30, 2026.
U.S. Appl. No. 17/954,096, filed Sep. 27, 2022 Notice of Allowance dated Apr. 23, 2026.
U.S. Appl. No. 18/075,261, filed Dec. 5, 2022 Non-Final Office Action dated Apr. 22, 2026.
US 18/099, 185 filed Jan. 19, 2023 Final Office Action dated Apr. 20, 2026.
U.S. Appl. No. 18/383,814, filed Oct. 25, 2023 Non-Final Office Action dated Apr. 17, 2026.
U.S. Appl. No. 18/593,431, filed Mar. 1, 2024 Non-Final Office Action dated Apr. 21, 2026.

* cited by examiner 132
138
116
108
102

RAPIDLY INSERTABLE CENTRAL CATHETERS INCLUDING CATHETER ASSEMBLIES AND METHODS THEREOF

PRIORITY

This application claims the benefit of priority to U.S. Patent Application No. 63/016,085, filed Apr. 27, 2020, which is incorporated by reference in its entirety into this application.

BACKGROUND

A central venous catheter ("CVC") is formed of a material having a relatively low durometer, which contributes to the CVC having a lack of column strength. Due to the lack of column strength, CVCs are commonly introduced into patients and advanced through their vasculatures by way of the Seldinger technique. The Seldinger technique utilizes a number of steps and medical devices (e.g., a needle, a scalpel, a guidewire, an introducer sheath, a dilator, a CVC, etc.). While the Seldinger technique is effective, the number of steps are time consuming, handling the number of medical devices is awkward, and both of the foregoing can lead to patient trauma. In addition, there is a relatively high potential for touch contamination due to the number of medical devices that need to be interchanged during the number of steps of the Seldinger technique. As such, there is a need to reduce the number of steps and medical devices involved in introducing a catheter such as a CVC into a patient and advancing the catheter through a vasculature thereof.

Disclosed herein are rapidly insertable central catheters ("RICCs") including catheter assemblies and methods thereof that address the foregoing.

SUMMARY

Disclosed herein is a RICC assembly including, in some embodiments, a RICC, an introducer, and a coupling system configured to couple the RICC and the introducer together. The RICC includes a catheter tube, a catheter hub, and one or more extension legs. The catheter tube includes a side aperture through a side of the catheter tube in a distal-end portion thereof. The side aperture opens into an introducing lumen of the catheter tube that extends from at least the side aperture to a distal end of the RICC. The catheter hub is coupled to a proximal-end portion of the catheter tube. Each extension leg of the one-or-more extension legs is coupled to the catheter hub by a distal-end portion thereof. The introducer includes an introducer needle having a cannula. The coupling system includes a distal coupler slidably attached to the catheter tube proximal of the side aperture. The cannula extends through a longitudinal through hole of the distal coupler, through the side aperture of the catheter tube, along the introducing lumen of the catheter tube, and through the distal end of the RICC when the RICC assembly is in a ready-to-deploy state thereof.

In some embodiments, the cannula of the introducer needle extends at least about 2-7 cm from the distal end of the RICC in the ready-to-deploy state of the RICC for a venipuncture with the cannula.

In some embodiments, the distal coupler includes a tab configured to allow a clinician to single handedly advance the RICC off the cannula with a single finger of a hand while holding the guidewire conduit between a thumb and another finger or fingers of the hand.

In some embodiments, the introducer further includes a guidewire conduit and an access guidewire disposed in the guidewire conduit. The guidewire conduit is coupled to a needle hub of the introducer needle. The guidewire conduit is configured to maintain sterility of the access guidewire.

In some embodiments, the guidewire conduit includes a longitudinal slit and the access guidewire includes a handle coupled to a proximal-end portion of the access guidewire. The handle protrudes through the longitudinal slit for grasping the handle and advancing the access guidewire through the distal end of the RICC without directly touching the access guidewire.

In some embodiments, the longitudinal slit includes closed ends configured to provide stops for the handle. The stops prevent loss of the access guidewire in a blood-vessel lumen of a patient by over advancement of the access guidewire. The stops also prevent withdrawal of the access guidewire from the guidewire conduit by over withdrawal of the access guidewire.

In some embodiments, the introducer further includes a fluid-pressure indicator extending from a side arm of the needle hub. The fluid-pressure indicator is fluidly coupled to a needle lumen of the introducer needle by way of a side-arm lumen of the side arm for observing blood flashback.

In some embodiments, the coupling system further includes a proximal coupler removably attached to the catheter hub and slidably attached to the guidewire conduit. The coupling system is configured to couple the RICC and the introducer together by corresponding proximal-end and distal-end portions thereof in the ready-to-deploy state of the RICC assembly while allowing the introducer to slide relative to the RICC.

In some embodiments, the proximal coupler includes sloped sides configured to push the guidewire conduit out of the proximal coupler when a proximal coupler-interacting portion of the introducer interacts with the sloped sides while the cannula is withdrawn from the side aperture of the catheter tube.

In some embodiments, the proximal coupler includes posts and the catheter hub includes a suture wing with suture-wing holes. The posts are disposed in the suture-wing holes in the ready-to-deploy state of the RICC assembly.

In some embodiments, the RICC further includes a sterile barrier over the catheter tube between the proximal coupler and the distal coupler to which the sterile barrier is coupled. The sterile barrier is configured to split apart when the proximal coupler is removed from the catheter hub and the sterile barrier is pulled away from the catheter tube.

In some embodiments, the sterile barrier has sufficient tensile strength to pull the distal coupler off the catheter tube without breaking when the sterile barrier splits down to the distal coupler while being pulled away from the catheter tube.

In some embodiments, the RICC includes a set of three lumens including a distal lumen, a medial lumen, and a proximal lumen formed of fluidly connected portions of three catheter-tube lumens, three hub lumens, and three extension-leg lumens. The introducing lumen of the catheter tube is coincident with a distal-end portion of the distal lumen.

In some embodiments, the distal lumen has a distal-lumen aperture in a distal end of the RICC, the medial lumen has a medial-lumen aperture in the side of the catheter tube distal of the side aperture, and the proximal lumen has a proximal-lumen aperture in the side of the catheter tube distal of the side aperture but proximal of the medial-lumen aperture.

Also disclosed herein is a method for inserting a RICC into a blood-vessel lumen of a patient including a RICC assembly-obtaining step, needle tract-establishing step, a first catheter-advancing step; and a cannula-withdrawing step. The RICC assembly-obtaining step obtaining a RICC assembly including the RICC, an introducer including an introducer needle, and a coupling system including a distal coupler that couples the RICC and the introducer together by distal-end portions thereof in a ready-to-deploy state of the RICC assembly. The needle tract-establishing step includes establishing a needle tract from an area of skin to the blood-vessel lumen of the patient with a cannula of the introducer needle. The cannula extends through a longitudinal through hole of the distal coupler, through a side aperture in a distal-end portion of a catheter tube of the RICC, along an introducing lumen of the catheter tube, and out a distal end of the RICC. The first catheter-advancing step includes advancing the distal-end portion of the catheter tube into the blood-vessel lumen over the cannula. The cannula-withdrawing step includes withdrawing the cannula from the introducing lumen by way of the side aperture of the catheter tube.

In some embodiments, the method further includes cannula-ensuring step of ensuring the cannula extends at least about 2-7 cm beyond the distal end of the RICC before the needle tract-establishing step.

In some embodiments, the needle tract-establishing step includes ensuring blood flashes back into a needle hub of the introducer needle, a side arm of the needle hub, or a fluid-pressure indicator extending from the side arm of the needle hub.

In some embodiments, the method further includes an access guidewire-advancing step of advancing an access guidewire by a handle coupled to a proximal-end portion of the access guidewire into the blood-vessel lumen beyond a distal end of the cannula. The handle protrudes through a longitudinal slit in a guidewire conduit coupled to the introducer needle.

In some embodiments, the first catheter-advancing step includes advancing the catheter tube into the blood-vessel lumen with a single finger of a hand while holding the guidewire conduit between a thumb and another finger or fingers of the hand. The distal coupler includes a tab configured for advancing the catheter tube into the blood-vessel lumen with the single finger.

In some embodiments, the first catheter-advancing step includes advancing the catheter tube into the blood-vessel lumen until a proximal coupler of the coupling system slidably attached to the guidewire conduit pushes the guidewire conduit out of the proximal coupler. The introducer includes a proximal coupler-interacting portion configured to interact with sloped sides of the proximal coupler and push the guidewire conduit out of the proximal coupler.

In some embodiments, the method further includes a maneuver guidewire-advancing step of advancing a maneuver guidewire into the blood-vessel lumen by way of a distal lumen having a distal-lumen aperture in the distal end of the RICC. The introducing lumen of the catheter tube is coincident with a distal-end portion of the distal lumen.

In some embodiments, the method further includes a second catheter-advancing step of advancing the distal-end portion of the catheter tube further into the blood-vessel lumen over the maneuver guidewire. Concomitantly, the second catheter-advancing step includes sliding the distal coupler proximally towards the proximal coupler to uncover the catheter tube. The catheter tube is covered by a sterile barrier between the proximal coupler and the distal coupler in a ready-to-deploy state of the RICC assembly.

In some embodiments, the method further includes a sterile barrier-removing step of removing the sterile barrier and a remainder of the coupling system from the RICC. The sterile barrier-removing step includes removing the proximal coupler from a catheter hub of the RICC, pulling the sterile barrier away from the catheter tube to split the sterile barrier apart, and removing the distal coupler from the catheter tube to which the distal coupler is slidably attached.

These and other features of the concepts provided herein will become more apparent to those of skill in the art in view of the accompanying drawings and following description, which describe particular embodiments of such concepts in greater detail.

DRAWINGS

DESCRIPTION

Figure 1:
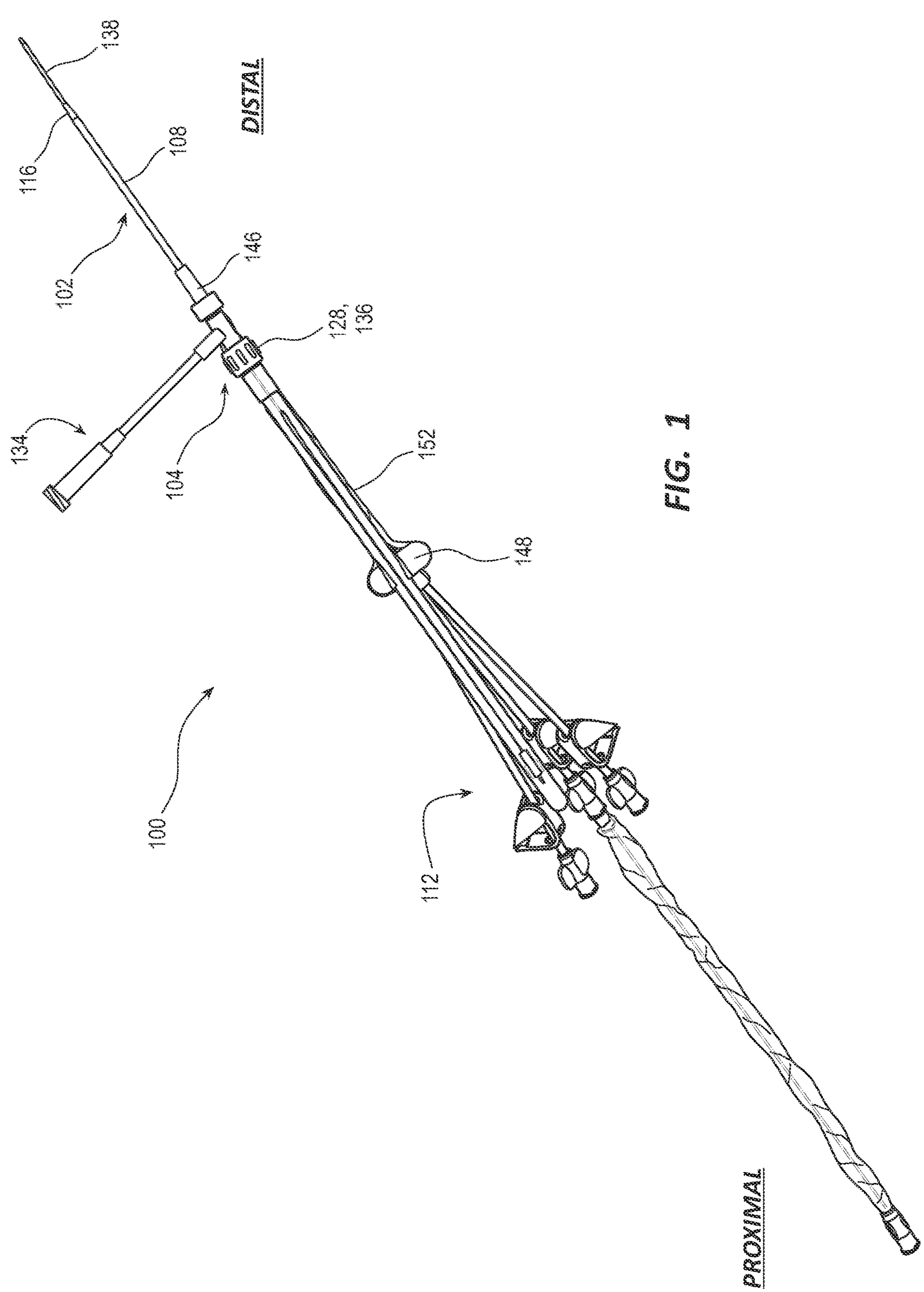
FIG. 1 illustrates a top view of a RICC assembly including a RICC, an introducer, and a coupling system in accordance with some embodiments.
Figure 2:
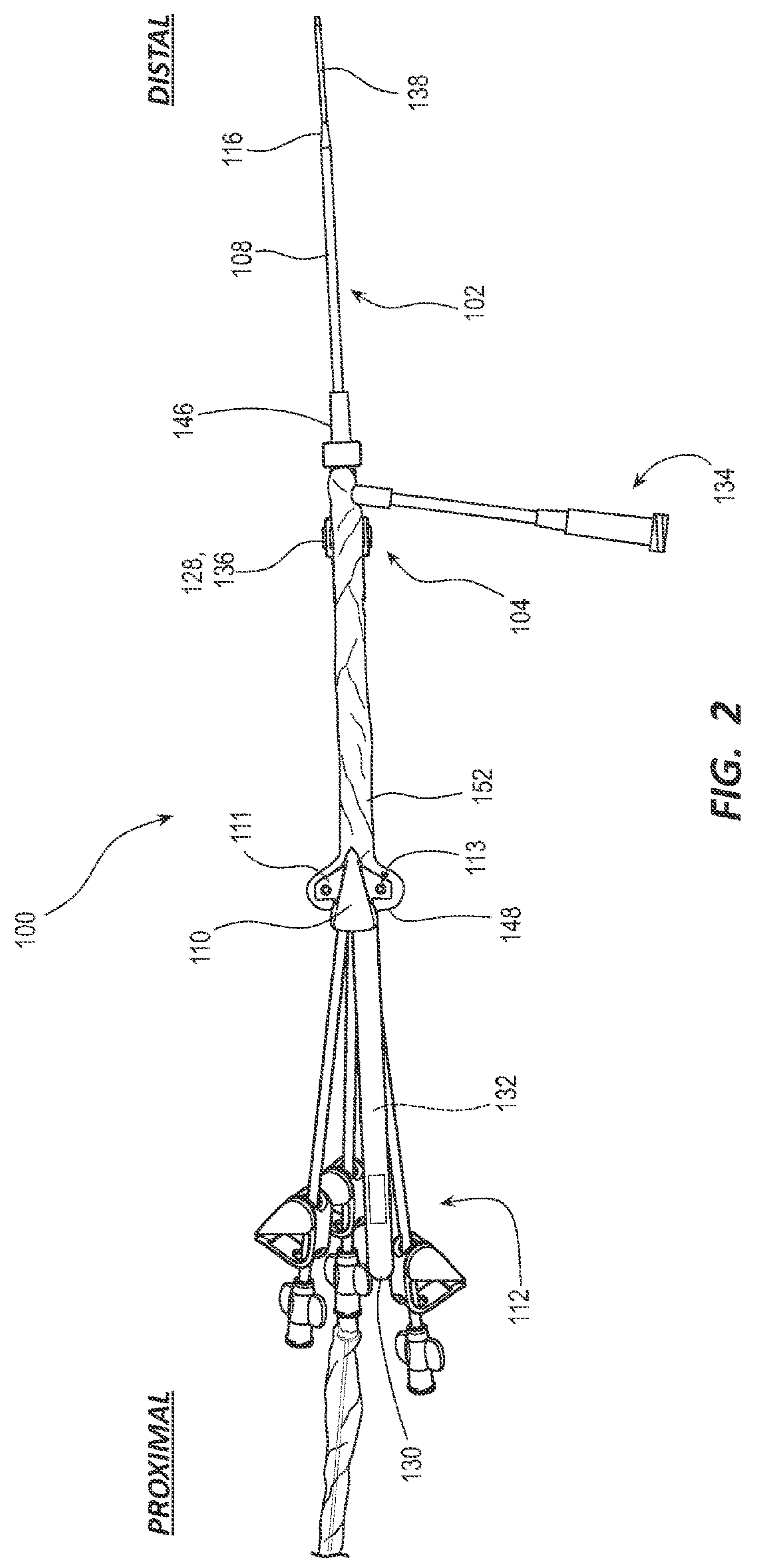
FIG. 2 illustrates a bottom view of the RICC assembly in accordance with some embodiments.
Figure 3:
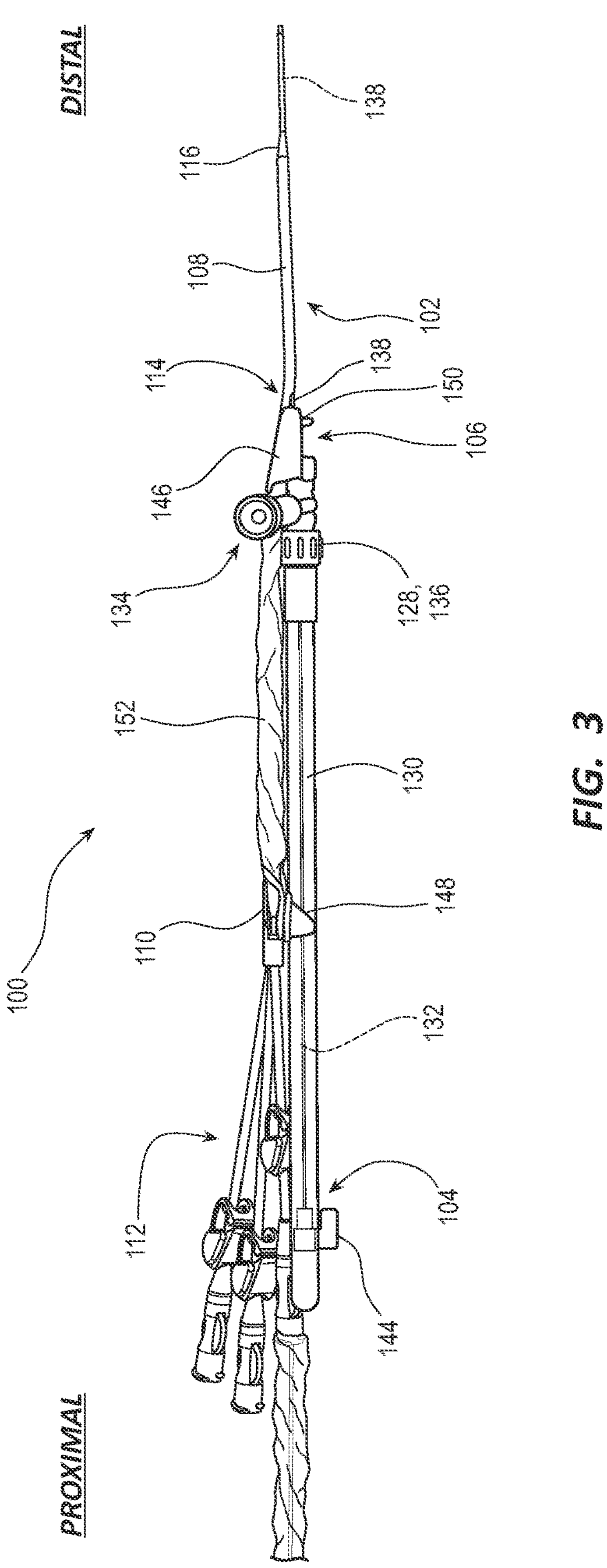
FIG. 3 illustrates a side view of the RICC assembly in accordance with some embodiments.
Figure 4:
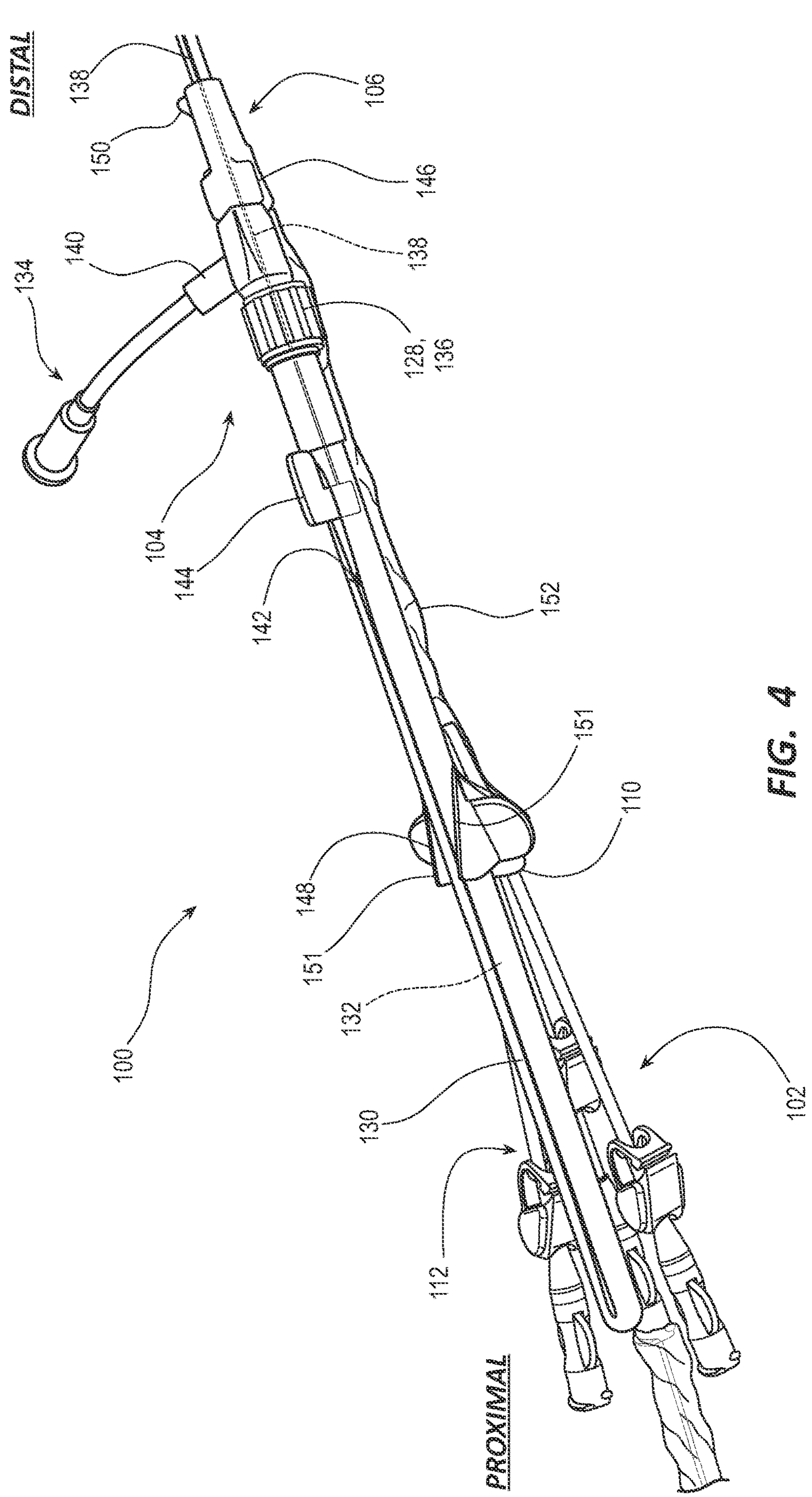
FIG. 4 illustrates a detailed top view of the RICC assembly in accordance with some embodiments.
Figure 5:
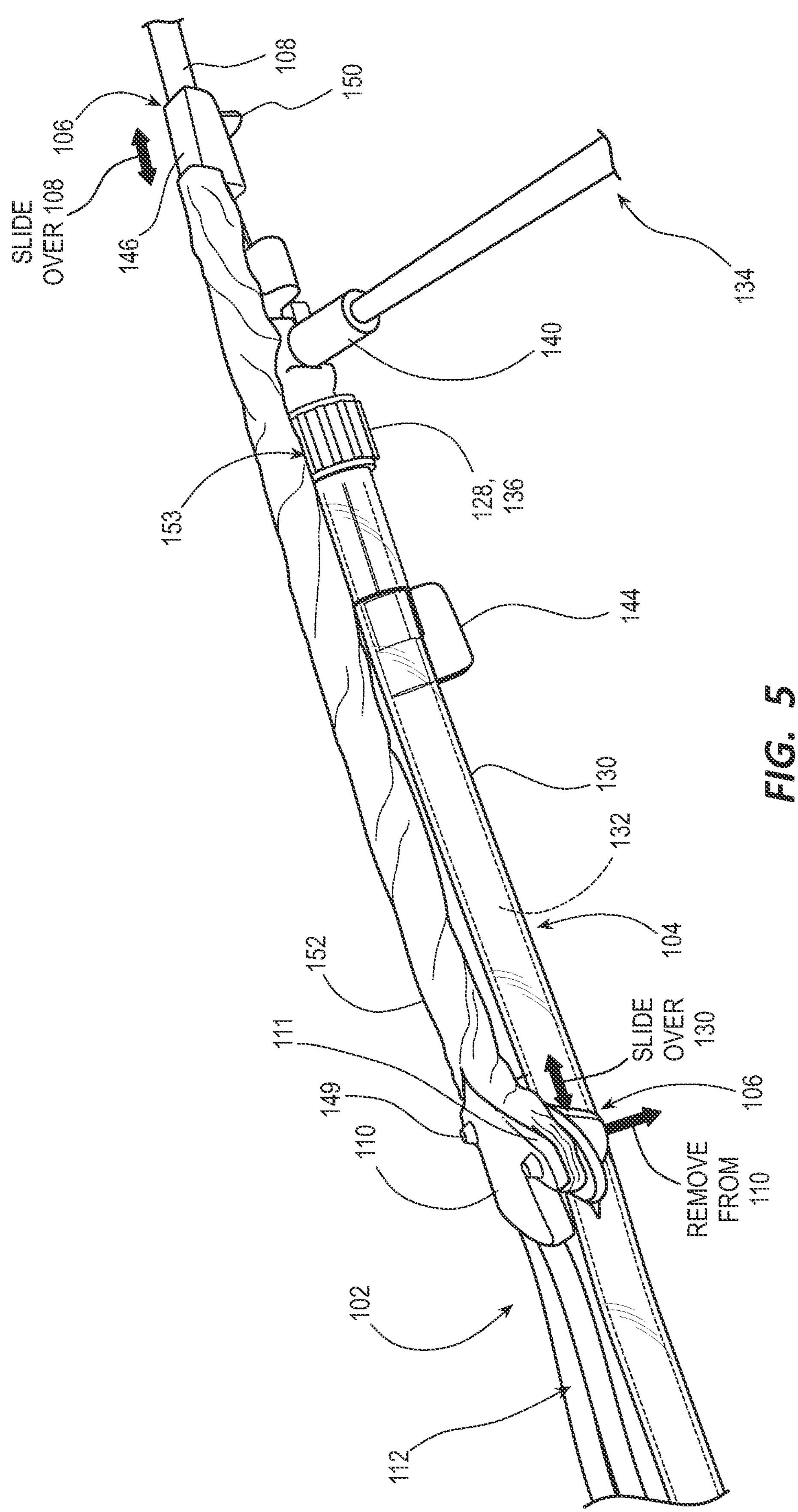
FIG. 5 illustrates a detailed side view of the RICC assembly in accordance with some embodiments.

Before some particular embodiments are disclosed in greater detail, it should be understood that the particular embodiments disclosed herein do not limit the scope of the concepts provided herein. It should also be understood that a particular embodiment disclosed herein can have features that can be readily separated from the particular embodiment and optionally combined with or substituted for features of any of a number of other embodiments disclosed herein.

Regarding terms used herein, it should also be understood the terms are for the purpose of describing some particular embodiments, and the terms do not limit the scope of the concepts provided herein. Ordinal numbers (e.g., first, second, third, etc.) are generally used to distinguish or identify different features or steps in a group of features or steps, and do not supply a serial or numerical limitation. For example, "first," "second," and "third" features or steps need not necessarily appear in that order, and the particular embodiments including such features or steps need not necessarily be limited to the three features or steps. Labels such as "left," "right," "top," "bottom," "front," "back," and the like are used for convenience and are not intended to imply, for example, any particular fixed location, orientation, or direction. Instead, such labels are used to reflect, for example, relative location, orientation, or directions. Singular forms of "a," "an," and "the" include plural references unless the context clearly dictates otherwise.

With respect to "proximal," a "proximal portion" or a "proximal-end portion" of, for example, a catheter disclosed herein includes a portion of the catheter intended to be near a clinician when the catheter is used on a patient. Likewise, a "proximal length" of, for example, the catheter includes a length of the catheter intended to be near the clinician when the catheter is used on the patient. A "proximal end" of, for example, the catheter includes an end of the catheter intended to be near the clinician when the catheter is used on the patient. The proximal portion, the proximal-end portion, or the proximal length of the catheter can include the proximal end of the catheter; however, the proximal portion, the proximal-end portion, or the proximal length of the catheter need not include the proximal end of the catheter. That is, unless context suggests otherwise, the proximal portion, the proximal-end portion, or the proximal length of the catheter is not a terminal portion or terminal length of the catheter.

With respect to "distal," a "distal portion" or a "distal-end portion" of, for example, a catheter disclosed herein includes a portion of the catheter intended to be near or in a patient when the catheter is used on the patient. Likewise, a "distal length" of, for example, the catheter includes a length of the catheter intended to be near or in the patient when the catheter is used on the patient. A "distal end" of, for example, the catheter includes an end of the catheter intended to be near or in the patient when the catheter is used on the patient. The distal portion, the distal-end portion, or the distal length of the catheter can include the distal end of the catheter; however, the distal portion, the distal-end portion, or the distal length of the catheter need not include the distal end of the catheter. That is, unless context suggests otherwise, the distal portion, the distal-end portion, or the distal length of the catheter is not a terminal portion or terminal length of the catheter.

Unless defined otherwise, all technical and scientific terms used herein have the same meaning as commonly understood by those of ordinary skill in the art.

As set forth above, there is a need to reduce the number of steps and medical devices involved in introducing a catheter such as a CVC into a patient and advancing the catheter through a vasculature thereof Disclosed herein are rapidly insertable central catheters ("RICCs") including catheter assemblies and methods thereof that address the foregoing. However, it should be understood the RICCs are but one type of catheter in which the concepts provided herein can be embodied or otherwise incorporated. Indeed, peripherally inserted central catheters ("PICCs"), dialysis catheters, or the like can also embody or otherwise incorporate the concepts provided herein for the RICCs, as well as catheter assemblies and methods thereof.

RICC assemblies

Figure 6:
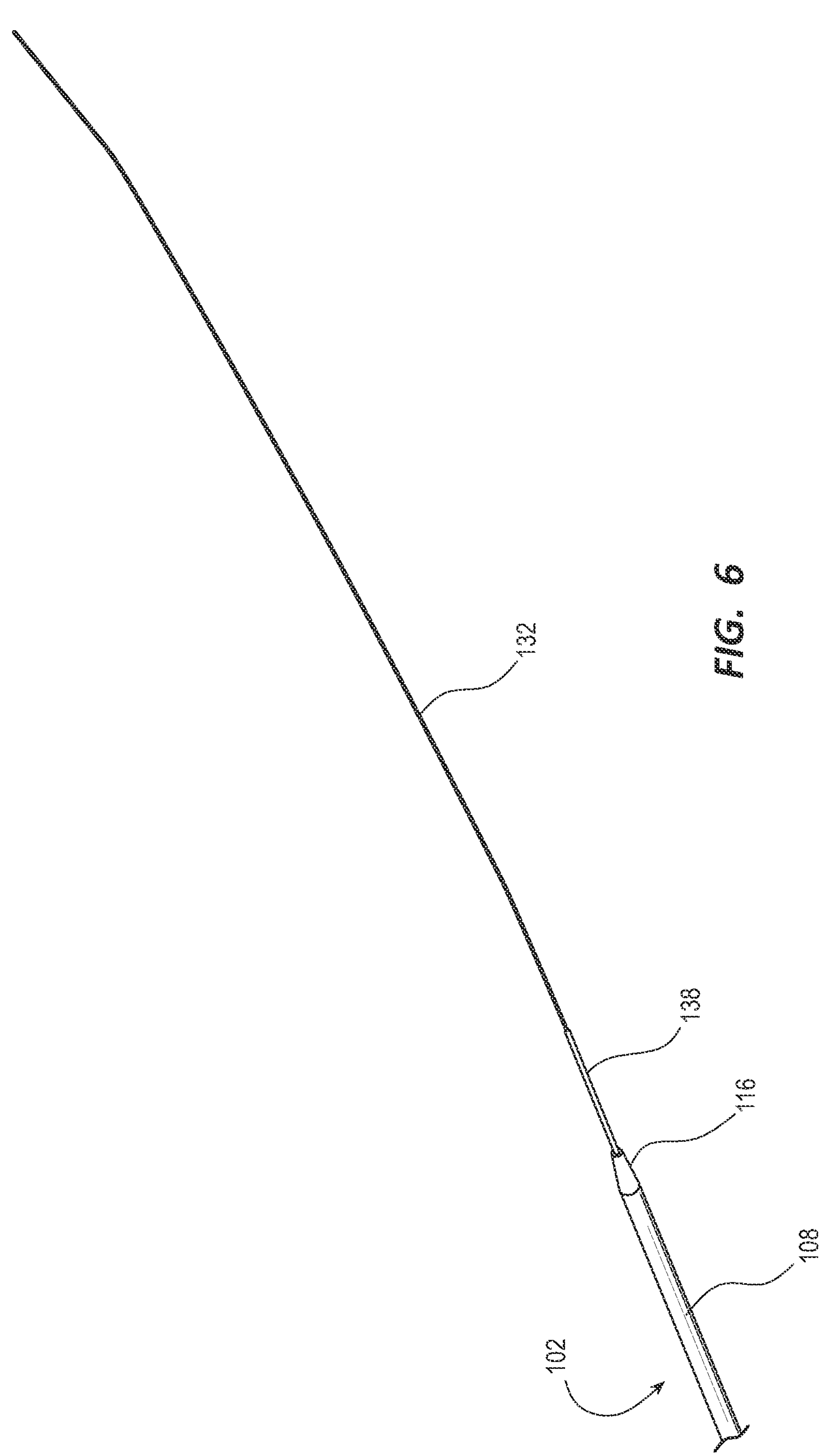
FIG. 6 illustrates a distal-end portion of the RICC assembly in accordance with some embodiments.
Figures 7, 8, 9:
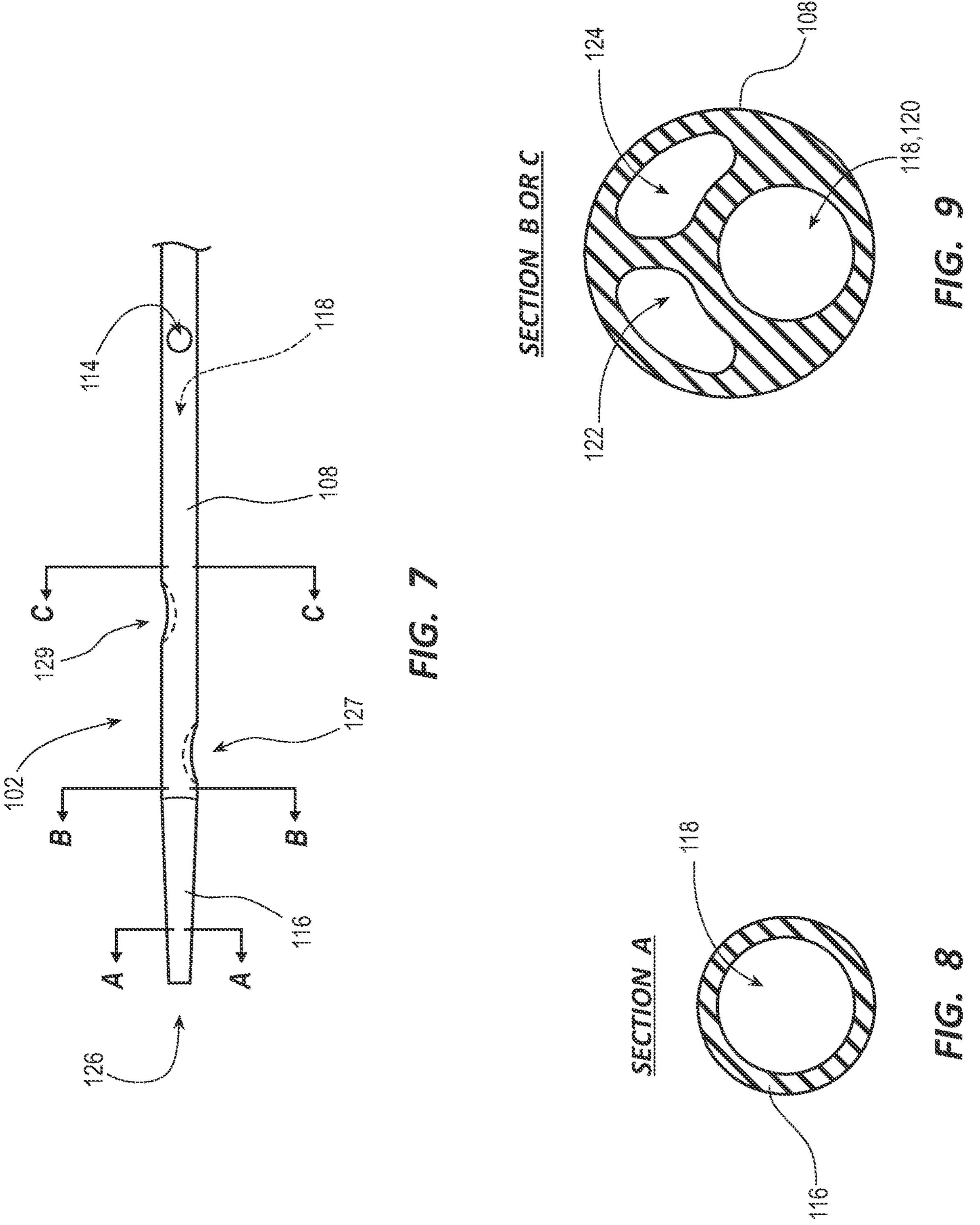
FIG. 7 illustrates a distal-end portion of a catheter tube of the RICC in accordance with some embodiments.
FIG. 8 illustrates a first transverse cross section of the catheter tube in accordance with some embodiments, the first transverse cross section labeled "Section A" in accordance with section lines A-A in FIG. 7.
FIG. 9 illustrates a second or third transverse cross section of the catheter tube in accordance with some embodiments, the second or third transverse cross section labeled "Section B or C" in accordance with section lines B-B or C-C in FIG. 7.

FIGS. 1-5 illustrate various views of a RICC assembly 100 including a RICC 102, an introducer 104, and a coupling system 106 in accordance with some embodiments. FIG. 6 illustrates a distal-end portion of the RICC assembly 100 in accordance with some embodiments. FIG. 7 illustrates a distal-end portion of a catheter tube 108 of the RICC 102 in accordance with some embodiments. FIGS. 8 and 9 illustrates various transverse cross-sections of the catheter tube 108 in accordance with some embodiments.

As shown, the RICC assembly 100 includes, in some embodiments, the RICC 102, the introducer 104, and the coupling system 106 configured to couple the RICC 102 and the introducer 104 together. The RICC 102, the introducer 104, and the coupling system 106 are described, in turn, in sections set forth below; however, some crossover between the sections for the RICC 102, the introducer 104, and the coupling system 106 exist in view of the interrelatedness of the RICC 102, the introducer 104, and the coupling system 106 in the RICC assembly 100.

The RICC 102 includes the catheter tube 108, a catheter hub 110, and one or more extension legs 112.

The catheter tube 108 includes one or more catheter-tube lumens, a side aperture 114 through a side of the catheter tube 108 in a distal-end portion of the catheter tube 108, and a tip 116 in the distal-end portion of the catheter tube 108.

The one-or-more catheter-tube lumens can extend through an entirety of the catheter tube 108; however, only one catheter-tube lumen typically extends from a proximal end of the catheter tube 108 to a distal end of the catheter tube 108 in a multiluminal RICC (e.g., a diluminal RICC, a triluminal RICC, a tetraluminal RICC, a pentaluminal RICC, a hexaluminal RICC, etc.). Indeed, the tip 116, typically includes a single lumen therethrough, whether or not the tip 116 is formed integrally with the catheter tube 108 or separately from the catheter tube 108 and coupled thereto. Optionally, the single lumen through the tip 116 can be referred to as a "tip lumen," particularly if the tip 116 is formed separately from the catheter tube 108 and coupled thereto, the latter of which effectively blocks all catheter-tube lumens at the distal end of the catheter tube 108 excepting that coaxially aligned with the tip lumen.

The side aperture 114 opens into an introducing lumen 118 of the one-or-more catheter-tube lumens. The introducing lumen 118 extends from at least the side aperture 114 to the distal end of the RICC 102 (e.g., the distal end of the catheter tube 108 or a distal end of the tip 116). The introducing lumen 118 is coincident with a distal-end portion of the one catheter-tube lumen set forth above that typically extends from the proximal end of the catheter tube 108 to the distal end of the catheter tube 108.

The catheter hub 110 is coupled to a proximal-end portion of the catheter tube 108. The catheter hub 110 includes one or more catheter-hub lumens corresponding in number to the one-or-more catheter-tube lumens. The one-or-more catheter-hub lumens extend through an entirety of the catheter hub 110 from a proximal end of the catheter hub 110 to a distal end of the catheter hub 110.

Each extension leg of the one-or-more extension legs 112 is coupled to the catheter hub 110 by a distal-end portion thereof. The one-or-more extension legs 112 respectively include one or more extension-leg lumens, which, in turn, correspond in number to the one-or-more catheter-tube lumens. Each extension-leg lumen of the one-or-more extension-leg lumens extends through an entirety of the extension leg from a proximal end of the extension leg to a distal end of the extension leg.

Each extension leg of the one-or-more extension legs 112 typically includes a Luer connector coupled to the extension leg, through which Luer connector the extension leg and the extension-leg lumen thereof can be connected to another medical device.

As shown, the RICC 102 can be triluminal including a set of three lumens. The set of three lumens includes, for example, a distal lumen 120, a medial lumen 122, and a proximal lumen 124 formed of fluidly connected portions of three catheter-tube lumens, three hub lumens, and three extension-leg lumens. The distal lumen 120 has a distal-lumen aperture 126 in the distal end of the RICC 102 (e.g., the distal end of the catheter tube 108 or a distal end of the tip 116), the medial lumen 122 has a medial-lumen aperture 127 in the side of the catheter tube 108 distal of the side aperture 114, and the proximal lumen 124 has a proximal-lumen aperture 129 in the side of the catheter tube 108 distal of the side aperture 114 but proximal of the medial-lumen aperture 127. The introducing lumen 118 of the catheter tube 108 is coincident with a distal-end portion of the distal lumen 120.

The introducer 104 includes an introducer needle 128 and a guidewire conduit 130 including an access guidewire 132 captively disposed in the guidewire conduit 130 to maintain sterility of the access guidewire 132. The introducer 104 can further include a fluid-pressure indicator 134 operably connected to the introducer needle 128.

The introducer needle 128 includes a needle hub 136 and a cannula 138 extending from the needle hub 136. The needle hub 136 is translucent and preferably colorless for observing blood flashback from a venipuncture with the cannula 138. When the RICC 102 is in a ready-to-deploy state of the RICC 102 as shown in FIGS. 1-5, the cannula 138 extends at least about 2-7 cm from the distal end of the RICC 102 for the venipuncture with the cannula 138. Indeed, the cannula 138 extends through the longitudinal through hole of the distal coupler 146 of the coupling system 106 set forth below, through the side aperture 114 of the catheter tube 108, along the introducing lumen 118 of the catheter tube 108, and through the distal end of the RICC 102 when the RICC assembly 100 is in the ready-to-deploy state thereof.

When present, the fluid-pressure indicator 134 extends from a side arm 140 of the needle hub 136. The fluid-pressure indicator 134 includes a closed end and an open end fluidly coupled to a needle lumen of the introducer needle 128 by way of a side-arm lumen of the side arm 140. The fluid-pressure indicator 134 is configured as a built-in accidental arterial indicator, wherein blood under sufficient pressure (e.g., arterial blood) can enter the fluid-pressure indicator 134 and compress a column of air within the fluid-pressure indicator 134. However, it is also possible to observe the blood flashback from the venipuncture with the cannula 138 in the fluid-pressure indicator 134.

The guidewire conduit 130 includes a closed proximal end and a distal-end portion coupled to the needle hub 136 of the introducer needle 128. The guidewire conduit 130 also includes a closed-ended longitudinal slit 142. The access guidewire 132 includes a handle 144 coupled to a proximal-end portion of the access guidewire 132. The handle 144 protrudes through the longitudinal slit 142 for grasping the handle 144 and advancing a distal-end portion of the access guidewire 132 through a distal-end portion of the cannula 138 where the access guidewire 132 resides (e.g., just short of a bevel of the cannula 138) in the ready-to-deploy state of the RICC 102. The foregoing components of the introducer 104 thusly provide a no-touch mechanism for advancing the access guidewire 132 into the blood-vessel lumen of the patient upon establishing a needle tract thereto. The foregoing components of the introducer 104 also provide a no-touch mechanism for withdrawing the access guidewire 132 from the blood-vessel lumen of the patient, for example, after the catheter tube 108 has been advanced over the access guidewire 132. Advantageously, the closed ends of the longitudinal slit 142 provide stops for the handle 144 protruding through the longitudinal slit 142. The stops prevent the access guidewire 132 from being lost in the blood-vessel lumen of the patient by over advancement of the access guidewire 132, and the stops prevent the access guidewire 132 from being pulled out of the guidewire conduit 130 by over withdrawal of the access guidewire 132, which mitigates contamination.

The coupling system 106 includes a distal coupler 146 and a proximal coupler 148 configured to couple the RICC 102 and the introducer 104 together by corresponding proximal-end and distal-end portions thereof in the ready-to-deploy state of the RICC assembly 100 while allowing the introducer 104 to slide relative to the RICC 102 (or vice versa).

The distal coupler 146 is slidably attached to the catheter tube 108 proximal of the side aperture 114. The cannula 138 extends through a longitudinal through hole of the distal coupler 146, through the side aperture 114 of the catheter tube 108, along the introducing lumen 118 of the catheter tube 108, and through the distal end of the RICC 102 when the RICC assembly 100 is in a ready-to-deploy state thereof. The distal coupler 146 includes a tab 150 configured to allow a clinician to single handedly advance the RICC 102 off the cannula 138 with a single finger of a hand (e.g., with a flick-type motion of the finger) while holding the guidewire conduit 130 between a thumb and another finger or fingers of the same hand, thereby providing a no-touch mechanism for advancing the RICC 102, specifically the distal-end portion of the catheter tube 108, over the cannula 138 and into the blood-vessel lumen of the patient.

The proximal coupler 148 is removably attached to the catheter hub 110 and slidably attached to the guidewire conduit 130. Indeed, the proximal coupler 148 includes posts 149 and the catheter hub 110 includes a suture wing 111 with suture-wing holes 113. The posts 149 of the proximal coupler 148 are disposed in the suture-wing holes 113 of the catheter hub 110 in the ready-to-deploy state of the RICC assembly 100. The proximal coupler 148 also includes sloped sides 151 configured to push the guidewire conduit 130 out of the proximal coupler 148 when a proximal coupler-interacting portion 153 of the introducer 104 (e.g., the needle hub 136 of the introducer needle 128, a wider portion of the guidewire conduit 130 such as a coupling that couples the guidewire conduit 130 to the needle hub 136, etc.) interacts with the sloped sides 151 while the cannula 138 is withdrawn from the side aperture 114 of the catheter tube 108.

The RICC 102 can further includes a sterile barrier 152 (e.g., a bag, a casing, etc.) configured to maintain sterility of the catheter tube 108 between the distal and proximal couplers 146 and 148 prior to insertion of the catheter tube 108 into the blood-vessel lumen of the patient. In the ready-to-deploy state of the RICC assembly 100, the sterile barrier 152 is over the catheter tube 108, between the distal coupler 146 and the proximal coupler 148, and coupled to the distal and proximal couplers 146 and 148. The sterile barrier 152 is configured to split apart when the proximal coupler 148 is removed from the catheter hub 110 and the sterile barrier 152 is pulled away from the catheter tube 108, thereby providing a no-touch mechanism for removing the sterile barrier 152 from the catheter tube 108. The sterile barrier 152 has sufficient tensile strength to pull the distal coupler 146 off the catheter tube 108 without breaking when the sterile barrier 152 splits down to the distal coupler 146 while being pulled away from the catheter tube 108.

Methods

A method of the RICC assembly 100 includes a method for inserting the RICC 102 into a blood-vessel lumen of a patient. Such a method includes, in some embodiments, a RICC assembly-obtaining step, a needle tract-establishing step, a first catheter-advancing step; and a cannula-withdrawing step.

The RICC assembly-obtaining step includes obtaining the RICC assembly 100. As set forth above, the RICC assembly 100 includes the RICC 102, the introducer 104 including the introducer needle 128, and the coupling system 106 including the distal coupler 146 that couples the RICC 102 and the introducer 104 together by the distal-end portions thereof in the ready-to-deploy state of the RICC assembly 100.

The method can further include a cannula-ensuring step of ensuring the cannula 138 extends at least about 2-7 cm beyond the distal end of the RICC 102 before the needle tract-establishing step. As set forth above, the cannula 138 extends through the longitudinal through hole of the distal coupler 146, through the side aperture 114 in the distal-end portion of the catheter tube 108 of the RICC 102, along the introducing lumen 118 of the catheter tube 108, and out the distal end of the RICC 102.

The needle tract-establishing step includes establishing a needle tract from an area of skin to the blood-vessel lumen of the patient with the cannula 138 of the introducer needle 128. The needle tract-establishing step can also include ensuring blood flashes back into the needle hub 136 of the introducer needle 128, the side arm 140 of the needle hub 136, or the fluid-pressure indicator 134 extending from the side arm 140 of the needle hub 136.

The method can further include an access guidewire-advancing step of advancing the access guidewire 132 by the handle 144 into the blood-vessel lumen beyond the distal end of the cannula 138. As set forth above, the handle 144 is coupled to the proximal-end portion of the access guidewire 132 and protrudes through the longitudinal slit 142 in the guidewire conduit 130, which is coupled to the introducer needle 128. The access guidewire-advancing step should be performed before the first catheter-advancing step such that the distal-end portion of the catheter tube 108 can be advanced over the access guidewire 132 as well. The access guidewire 132 provides the catheter tube 108 columnar strength for the first catheter-advancing step.

The first catheter-advancing step includes advancing the distal-end portion of the catheter tube 108 into the blood-vessel lumen over the cannula 138. For example, the first catheter-advancing step can include advancing the catheter tube 108 into the blood-vessel lumen with a single finger of a hand (e.g., with a flick-type motion of the finger) while holding the guidewire conduit 130 between a thumb and another finger or fingers of the same hand. The distal coupler 146 includes the tab 150 configured for advancing the catheter tube 108 into the blood-vessel lumen with the single finger.

The first catheter-advancing step can also include advancing the catheter tube 108 into the blood-vessel lumen until the proximal coupler 148 of the coupling system 106 pushes the guidewire conduit 130 out of the proximal coupler 148. As set forth above, the introducer 104 includes the proximal coupler-interacting portion 153 (e.g., the needle hub 136 of the introducer needle 128, a wider portion of the guidewire conduit 130 such as a coupling that couples the guidewire conduit 130 to the needle hub 136, etc.) configured to interact with the sloped sides 151 of the proximal coupler 148 and push the guidewire conduit 130 out of the proximal coupler 148.

The method can further include an access guidewire-withdrawing step of withdrawing the access guidewire 132 by the handle 144 into the guidewire conduit 130. The access guidewire-withdrawing step can be performed after the first catheter-advancing step such as after the distal-end portion of the catheter tube 108 is suitably placed within the blood-vessel lumen over both the cannula 138 and the access guidewire 132.

The cannula-withdrawing step includes withdrawing the cannula 138 from the introducing lumen 118 by way of the side aperture 114 of the catheter tube 108. Like the access guidewire-withdrawing step, the cannula-withdrawing step can be performed after the first catheter-advancing step such as after the distal-end portion of the catheter tube 108 is suitably placed within the blood-vessel lumen over both the cannula 138 and the access guidewire 132.

The method can further include an introducer-removing step of completely removing the introducer 104 from the RICC assembly 100 after the guidewire conduit 130 is pushed out of the proximal coupler 148. The cannula-withdrawing step can be part of the introducer-removing step.

The method can further include a maneuver guidewire-advancing step of advancing a maneuver guidewire into the blood-vessel lumen by way of, for example, the distal-lumen aperture 126 in the distal end of the RICC 102. As set forth above, the introducing lumen 118 of the catheter tube 108 is coincident with the distal-end portion of the distal lumen 120. As such, the introducer-removing step of completely removing the introducer 104 from the RICC assembly 100 should be performed before the maneuver guidewire-advancing step to ensure the distal lumen, or the introducing lumen 118 thereof, is free of both the cannula 138 and the access guidewire 132. That said, the maneuver guidewire-advancing step can be partially performed before the introducer-removing step. For example, the maneuver guidewire-advancing step can include a maneuver guidewire-loading step of loading the maneuver guidewire into the distal lumen 120 without advancing the maneuver guidewire into the portion of the distal lumen 120 coincident with the introducing lumen 118.

The maneuver guidewire of the maneuver guidewire-advancing step can have a length sufficient for advancing the catheter tube 108 of the RICC 102 to the lower ⅓ of the superior vena cava ("SVC") of the heart. The maneuver guidewire can be part of a guidewire management device configured to maintain sterility of the maneuver guidewire and facilitate the maneuver guidewire-advancing step. Alternatively, the maneuver guidewire is a stand-alone maneuver guidewire packaged in a sterile barrier (e.g., a bag, a casing, etc.) configured to maintain sterility of the maneuver guidewire. Such a maneuver guidewire can include a stopping means to stop advancement of the maneuver guidewire during the maneuver guidewire-advancing step, which obviates losing the maneuver guidewire in the patient. The stopping means can be a ball, a slug, or the like coupled to a proximal-end portion of the maneuver guidewire configured to not pass through, for example, the Luer connector of the extension leg in which at least the proximal-end portion of the maneuver guidewire is disposed during the maneuver guidewire-advancing step.

The method can further include a second catheter-advancing step of advancing the distal-end portion of the catheter tube 108 further into the blood-vessel lumen over the maneuver guidewire such as to the SVC. Concomitantly, the second catheter-advancing step includes sliding the distal coupler 146 proximally towards the proximal coupler 148 to uncover the catheter tube 108. As set forth above, the catheter tube 108 is covered by the sterile barrier 152 between the proximal coupler 148 and the distal coupler 146 in the ready-to-deploy state of the RICC assembly 100.

The method can further include a sterile barrier-removing step of removing the sterile barrier 152 and a remainder of the coupling system 106 from the RICC 102. The sterile barrier-removing step includes removing the proximal coupler 148 from the catheter hub 110 of the RICC 102 (e.g., pulling the posts 149 of the proximal coupler out of the suture-wing holes 113 of the catheter hub 110), pulling the sterile barrier 152 away from the catheter tube 108 to split the sterile barrier 152 apart along its length, and removing the distal coupler 146 from the catheter tube 108 to which the distal coupler 146 is slidably attached.

The method can further include a maneuver guidewire-withdrawing step of withdrawing the maneuver guidewire from the blood-vessel lumen of the patient, as well as withdrawing the maneuver guidewire from the RICC 102.

While some particular embodiments have been disclosed herein, and while the particular embodiments have been disclosed in some detail, it is not the intention for the particular embodiments to limit the scope of the concepts provided herein. Additional adaptations and/or modifications can appear to those of ordinary skill in the art, and, in broader aspects, these adaptations and/or modifications are encompassed as well. Accordingly, departures may be made from the particular embodiments disclosed herein without departing from the scope of the concepts provided herein.

What is claimed is:

1. A rapidly insertable central catheter ("RICC") assembly, comprising:

- a RICC including:
  - a catheter tube including a side aperture through a side of the catheter tube in a distal-end portion thereof, the side aperture opening into an introducing lumen of the catheter tube that extends from at least the side aperture to a distal end of the RICC;
  - a catheter hub coupled to a proximal-end portion of the catheter tube; and
  - one or more extension legs, each extension leg of the one or more extension legs coupled to the catheter hub by a distal-end portion thereof;
- an introducer including an introducer needle having a needle hub and a cannula; and
- a coupling system including a distal coupler slidably attached to the catheter tube proximal of the side aperture; the cannula extending from the needle hub through a longitudinal through hole of the distal coupler, through the side aperture of the catheter tube, along the introducing lumen of the catheter tube, and through the distal end of the RICC when the RICC assembly is in a ready-to-deploy state thereof, the distal coupler including a tab configured to allow a clinician to single handedly advance the RICC off the cannula with a flick-type motion of a single finger of a hand while holding the introducer between a thumb and another finger or fingers of the hand, the RICC assembly thereby providing a mechanism for advancing the RICC without touching the catheter tube.

2. The RICC assembly of claim 1, wherein the cannula of the introducer needle extends at least about 2-7 cm from the distal end of the RICC in the ready-to-deploy state of the RICC for a venipuncture with the cannula.

3. The RICC assembly of claim 1, the introducer further including:

- a guidewire conduit coupled to the needle hub of the introducer needle; and
- an access guidewire disposed in the guidewire conduit, the guidewire conduit configured to maintain sterility of the access guidewire.

4. The RICC assembly of claim 3, wherein the guidewire conduit includes a longitudinal slit and the access guidewire includes a handle coupled to a proximal-end portion of the access guidewire, the handle protruding through the longitudinal slit for grasping the handle and advancing the access guidewire through the distal end of the RICC without directly touching the access guidewire.

5. The RICC assembly of claim 4, wherein the longitudinal slit includes closed ends configured to provide stops for the handle that prevent loss of the access guidewire in a blood-vessel lumen of a patient by over advancement of the access guidewire or withdrawal of the access guidewire from the guidewire conduit by over withdrawal of the access guidewire.

6. The RICC assembly of claim 3, the introducer further including a fluid-pressure indicator extending from a side arm of the needle hub, the fluid-pressure indicator fluidly coupled to a needle lumen of the introducer needle by way of a side-arm lumen of the side arm for observing blood flashback.

7. The RICC assembly of claim 3, the coupling system further including a proximal coupler removably attached to the catheter hub and slidably attached to the guidewire conduit, the coupling system configured to couple the RICC and the introducer together by corresponding proximal-end and distal-end portions thereof in the ready-to-deploy state of the RICC assembly while allowing the introducer to slide relative to the RICC.

8. The RICC assembly of claim 7, wherein the proximal coupler includes sloped sides configured to push the guidewire conduit out of the proximal coupler when a proximal coupler-interacting portion of the introducer interacts with the sloped sides while the cannula is withdrawn from the side aperture of the catheter tube.

9. The RICC assembly of claim 7, wherein the proximal coupler includes posts and the catheter hub includes a suture wing with suture-wing holes, the posts disposed in the suture-wing holes in the ready-to-deploy state of the RICC assembly.

10. The RICC assembly of claim 7, the RICC further including a sterile barrier over the catheter tube between the proximal coupler and the distal coupler to which couplers the sterile barrier is coupled, the sterile barrier configured to split apart when the proximal coupler is removed from the catheter hub and the sterile barrier is pulled away from the catheter tube.

11. The RICC assembly of claim 10, wherein the sterile barrier has sufficient tensile strength to pull the distal coupler off the catheter tube without breaking the sterile barrier when the sterile barrier splits down to the distal coupler while being pulled away from the catheter tube.

12. The RICC assembly of claim 1, wherein the RICC includes a set of three lumens including a distal lumen, a medial lumen, and a proximal lumen, each lumen of the set of three lumens is formed of fluidly connected portions of a catheter-tube lumen, a hub lumen, and an extension-leg lumen, the introducing lumen of the catheter tube coincident with a distal-end portion of the distal lumen.

13. The RICC assembly of claim 12, wherein the distal lumen has a distal-lumen aperture in the distal end of the RICC, the medial lumen has a medial-lumen aperture in the side of the catheter tube distal of the side aperture, and the proximal lumen has a proximal-lumen aperture in the side of the catheter tube distal of the side aperture but proximal of the medial-lumen aperture.

14. A rapidly insertable central catheter ("RICC") assembly, comprising:

a RICC including a catheter tube having a side aperture through a side of the catheter tube in a distal-end portion thereof, the side aperture opening into an introducing lumen of the catheter tube that extends from at least the side aperture to a distal end of the RICC;

an introducer including an introducer needle having a needle hub and a cannula; and a coupling system including a distal coupler slidably attached to the catheter tube proximal of the side aperture; the cannula extending from the needle hub through a longitudinal through hole of the distal coupler, through the side aperture of the catheter tube, along the introducing lumen of the catheter tube, and through the distal end of the RICC in a ready-to-deploy state thereof, and the distal coupler slidably attached to the catheter tube proximal of the cannula through the side aperture of the catheter tube, the distal coupler allowing a clinician to advance the RICC off the cannula without touching the catheter tube.

15. The RICC assembly of claim 14, the introducer further including:

a guidewire conduit coupled to the needle hub of the introducer needle; and an access guidewire disposed in the guidewire conduit, the guidewire conduit configured to maintain sterility of the access guidewire.

16. The RICC assembly of claim 15, wherein the guidewire conduit includes a longitudinal slit and the access guidewire includes a handle coupled to a proximal-end portion of the access guidewire, the handle protruding through the longitudinal slit for grasping the handle and advancing the access guidewire through the distal end of the RICC without directly touching the access guidewire.

17. The RICC assembly of claim 16, wherein the longitudinal slit includes closed ends configured to provide stops for the handle that prevent loss of the access guidewire in a blood-vessel lumen of a patient by over advancement of the access guidewire or withdrawal of the access guidewire from the guidewire conduit by over withdrawal of the access guidewire.

18. The RICC assembly of claim 15, the introducer further including a fluid-pressure indicator extending from a side arm of the needle hub, the fluid-pressure indicator fluidly coupled to a needle lumen of the introducer needle by way of a side-arm lumen of the side arm for observing blood flashback.

19. The RICC assembly of claim 15, the coupling system further including a proximal coupler removably attached to a catheter hub of the RICC and slidably attached to the guidewire conduit, the coupling system configured to couple the RICC and the introducer together by corresponding proximal-end and distal-end portions thereof in the ready-to-deploy state of the RICC assembly while allowing the introducer to slide relative to the RICC.

20. The RICC assembly of claim 19, wherein the proximal coupler includes sloped sides configured to push the guidewire conduit out of the proximal coupler when a proximal coupler-interacting portion of the introducer interacts with the sloped sides while the cannula is withdrawn from the side aperture of the catheter tube.

21. The RICC assembly of claim 19, wherein the proximal coupler includes posts and the catheter hub includes a suture wing with suture-wing holes, the posts disposed in the suture-wing holes in the ready-to-deploy state of the RICC assembly.

22. The RICC assembly of claim 19, the RICC further including a sterile barrier over the catheter tube between the proximal coupler and the distal coupler to which couplers the sterile barrier is coupled, the sterile barrier configured to split apart when the proximal coupler is removed from the catheter hub and the sterile barrier is pulled away from the catheter tube.

23. The RICC assembly of claim 22, wherein the sterile barrier has sufficient tensile strength to pull the distal coupler off the catheter tube without breaking the sterile barrier when the sterile barrier splits down to the distal coupler while being pulled away from the catheter tube.

24. The RICC assembly of claim 14, wherein the RICC includes a set of three lumens including a distal lumen, a medial lumen, and a proximal lumen, the distal lumen having a distal-lumen aperture in the distal end of the RICC, the medial lumen having a medial-lumen aperture in the side of the catheter tube distal of the side aperture, and the proximal lumen having a proximal-lumen aperture in the side of the catheter tube distal of the side aperture but proximal of the medial-lumen aperture.

* * * * *